United States Patent

Sala et al.

[11] Patent Number: 5,827,881
[45] Date of Patent: Oct. 27, 1998

[54] DIESTERS OF CARBONIC ACID ENDOWED WITH ANTIVIRAL AND ANTI-INFLAMMATORY ACTIVITY

[75] Inventors: Alberto Sala; Giorgio Bertolini; Gianfranco Pavich; Fabrizio Marcucci; Gianni Gromo; Giuliana Porro, all of Sesto S. Giovanni, Italy

[73] Assignee: Italfarmaco S.P.A., Milano, Italy

[21] Appl. No.: 869,043

[22] Filed: Jun. 4, 1997

Related U.S. Application Data

[63] Continuation of Ser. No. 687,567, filed as PCT/EP95/00637, Feb. 22, 1996, published as WO95/23128, Aug. 31, 1995, abandoned.

[30] Foreign Application Priority Data

Feb. 28, 1994 [IT] Italy .................................. MI94A0349

[51] Int. Cl.$^6$ .................................................. A61K 31/265
[52] U.S. Cl. ............................................ 514/512; 558/276
[58] Field of Search ................................................ 514/512

[56] References Cited

U.S. PATENT DOCUMENTS 3,162,673 12/1964 Brotherton et al. ..................... 558/276
5,264,425 11/1993 Dal Pozzo et al. .................. 558/276 X

FOREIGN PATENT DOCUMENTS 3347072 7/1985 Germany .

OTHER PUBLICATIONS

Database CAPLUS on STN International, Chemical Abstracts Service, (Columbus, Ohio), Accession No. 1990:538509, abstract of DE 3347072, 1990.

Primary Examiner—Michael G. Ambrose
Attorney, Agent, or Firm—Walter H. Schneider

[57] ABSTRACT

Diesters of carbonic acid disubstituted with primary, secondary or tertiary amine groups, pharmaceutically acceptable salts thereof, and their use as antiviral and inti-inflammatory agents.

3 Claims, No Drawings

DIESTERS OF CARBONIC ACID ENDOWED WITH ANTIVIRAL AND ANTI-INFLAMMATORY ACTIVITY

This is a continuation of application Ser. No. 08/687,567 filed Aug. 9, 1996, now abandoned, which was filed under 35 USC 371 and is the national stage of PCT International Application No. PCT/EP95/00637, filed Feb. 22, 1996, published as WO95/23128 Aug. 31, 1995.

The present invention relates to diesters of carbonic acid disubstituted with primary, secondary or tertiary amine groups, to the pharmaceutically acceptable salts thereof, and to their use as antiviral and anti-inflammatory agents.

Some of the compounds of the present invention, wherein the amine groups are in form of free base, are described in EP-B-0 423 151, in the applicant's name, as compounds useful to salify glycosaminoglycanes and make them administrable through a nonparenteral route.

Thus the present invention relates to compounds of formula (I):

$$A-R-O-\underset{\underset{O}{\|}}{C}-O-R_1-A' \qquad (I)$$

wherein R and $R_1$ are independently methylene, ethylene, optionally branched ($C_{3-18}$)alkylene, optionally branched ($C_{2-10}$)alkylidene, ($C_{5-7}$)cycloalkylene, a group $$-(CH)_n-\underset{R_2}{\bigcirc}-(CH)_m-\underset{R_3}{}$$

wherein $R_2$ and $R_3$ are independently hydrogen or a ($C_{1-4}$) alkyl group, and n and m are independently 0 or an integer from 1 to 6; or R and $R_1$ may be independently absent; A and A' independently represent:

a) a group $$\underset{R_5}{\overset{R_4}{\diagdown}}N-$$

wherein $R_4$ and $R_5$ are independently hydrogen, optionally branched ($C_{1-14}$)alkyl, ($C_{3-7}$)cyclo-alkyl, phenyl or phenyl ($C_{1-4}$)alkyl, or $R_4$ and $R_5$ taken together with the nitrogen atom form a heterocycle of from 5 to 7 atoms, optionally containing another heteroatom selected from the group consisting of O, N and S, and said heterocycle may be optionally substituted by one or more ($C_{1-6}$)alkyl groups;

b) a basic aromatic heterocycle radical linked by a carbon atom;

c) a totally or partially hydrogenated basic heterocycle radical linked by a carbon atom and optionally substituted by one or more ($C_{1-6}$)alkyl groups; and the diastereoisomers and diastereoisomeric mixtures thereof for use as therapeutically active compounds, with the exclusion of the following compounds: bis(β-dimethylaminoethyl) carbonate, bis(β-diethylaminoethyl) carbonate, bis(A-dimethylaminobutyl) carbonate, bis(piperidino)ethyl carbonate, bis(morpholino) ethyl carbonate."

Another object of the present invention relates to the use of the compounds of formula (I), including the known ones, in the antiviral and anti-inflammatory therapy.

A further object of the invention relates to compounds of formula (I):

$$A-R-O-\underset{\underset{O}{\|}}{C}-O-R_1-A' \qquad (I)$$

wherein R and $R_1$ are independently methylene, ethylene, optionally branched ($C_{3-18}$)alkylene, optionally branched ($C_{2-10}$)alkylidene, ($C_{5-7}$)cycloalkylene, a group $$-(CH)_n-\underset{R_2}{\bigcirc}-(CH)_m-\underset{R_3}{}$$

wherein $R_2$ and $R_3$ are independently hydrogen or a ($C_{1-4}$) alkyl group, and n and m are independently 0 or an integer from 1 to 6; or R and $R_1$ may be independently absent; A and A' independently represent:

a) a group $$\underset{R_5}{\overset{R_4}{\diagdown}}N-$$

wherein $R_4$ and $R_5$ independently are hydrogen, optionally branched ($C_{1-14}$)alkyl, ($C_{3-7}$)cycloalkyl, phenyl or phenyl($C_{1-4}$)alkyl, or $R_4$ and $R_5$ taken together with the nitrogen atom form a heterocycle of from 5 to 7 atoms, optionally containing another heteroatom selected from the group consisting of O, N and S, and said heterocycle may be optionally substituted by one or more ($C_{1-6}$)alkyl groups;

b) a basic aromatic heterocycle radical linked by a carbon atom;

c) a totally or partially hydrogenated basic heterocycle radical linked by a carbon atom and optionally substituted by one or more (C1–6)alkyl groups;

with the proviso that when R and $R_1$ are the same and represent ethylene, A and A' cannot be N-piperidyl, and $R_4$ and $R_5$ cannot be at the same time a radical selected from the group consisting of methyl, ethyl, butyl or hexyl; and when R and $R_1$ are the same and represent propylene or butylene, $R_4$ and $R_5$ cannot be at the same time a radical selected from the group consisting of methyl, butyl or hexyl; and the diastereoisomers and diastereoisomeric mixtures thereof.

Said compounds are novel and useful in the antiviral and anti-inflammatory therapy.

Another further object of the present invention relates to salts of formula (I'):

$$A-R-O-\underset{\underset{O}{\|}}{C}-O-R_1-A' \qquad (I')$$

wherein R, $R_1$ A and A' are as defined in formula (I), with pharmaceutically acceptable organic or inorganic acids; the diastereoisomers and diastereoisomeric mixtures thereof, and the relevant hydrate forms, with the exclusion of the following compounds: bis(B-diethylaminoethyl) carbonate dihydrochloride, bis(piperidino)ethyl carbonate dihydrochloride, bis(morpholino)oethyl carbonate dihydrochloride and bis(4-aminophenyl) carbonate dihydrochloride.

The salts of formula (I') are useful in the antiviral and anti-inflammatory therapy.

As intended below, alkyl groups essentially identify methyl, ethyl, propyl,- i-propyl, butyl, 2-methyl-propyl, n-pentyl, 3-methylbutyl, i-pentyl, n-hexyl, 2-methyl-pentyl, 2,3-dimethyl-butyl, n-heptyl, 3-ethyl-pentyl, 2,4-dimethyl-pentyl, n-octyl, 2-methylheptyl, 2,2,4-trimethyl-pentyl, nonyl, decyl, undecyl, dodecyl, trisdecyl, tetradecyl and the like, while a linear or branched $(C_{3-18})$alkylene represents, for example, 2-methylethylene, 1,3-propylene, 1,4-butylene, 2-ethylethylene, 3-methylpropylene, 1,5-pentylene, 2-ethylpropylene, 2-methylbutylene, 1,6-hexylene, 1-ethyl-1-methylpropylene, 3-methylpentylene, n-hepty-lene, 3-ethyl-pentylene, n-octylene, 2,2,4-trimethyl-pentylene, n-nonylene, n-decylene, undecylene, dodecylene, trisdecylene, tetradecylene, pentadecylene, hexadecylene, heptadecylene, octadecylene, and the like. A $(C_{2-10})$ alkylidene group mey be, e.g., ethylidene, propylidene, butylidene, isobutylidene, 2-methyl-butylidene, hexylidene, 2,3-dimethyl-butylidene, n-heptylidene, 2- or 3-ethyl-pentylidene, n-octylidene, 2,2,4-trimethyl-pentylidene, n-nonylidene, n-decylidene and the like.

A basic aromatic heterocyclic radical may be, for example, pyridine, quinoline, isoquinoline, pyrirridine, pyridazine, pyrazine, imidazole, pyrazole, quinoxaline, quinazoline.

A totally or partially hydrogenated basic heterocyclic radical may be, for example, piperidine, tetrahydroquinoline, tetrahydroisoquinoline, decahydroquinoline, decahydroisoquinoline, hexahydropyrimidine, hexahydropyridazine, piperazine, pyrrolidine, pyrroline, imidazoline, pyrrazoline, pyrrazolidine.

Examples of pharmaceutically acceptable organic or inorganic acids are benzenesulfonic, hydrobromic, camsilic, hydroiodic, hydrochloric, 1,2-ethane-disulfonic, laurilsulfonic, ethane-sulfonic, hydroxy-ethane-sulfonic, methanesulfonic, napsilic, nitric, phosphoric, sulforic acid.

The compounds of formula (I) may be prepared using methods known from the literature, e.g., the ones described in the already cited EP-B-0 423 151, starting from an aminoalkanol of general formula (II) or (II'):

A—R—OH (II)

A'—R1—OH (II')

wherein A, A', R and $R_1$ are as defined above. These reactants are commercially available or are described in literature [see, for example, Burford, R. R. et al., J. Chem. Soc., 2937–2942 (1957); Culberstun, T. P. et al., J. Med. Chem., 30, 1711–1715 (1987)], or also prepared according to schemes well known to the skilled in the field, or are easily derivable from the following examples provided hereinbelow.

When a compound of formula (I) which is a symmetric carbonate is desired, the due aminoalkanol of formula (II) or (II') is reacted in a double molar amount with carbonyldiimidazole in an inert solvent such as tetrahydrofuran, dioxane, polyhalogenated solvents, optionally in the presence of a catalytic amount of metallic sodium, at a temperature ranging between about 0° C. and about 50° C. for from about 2 to about 24 hours.

Specifically, when a symmetric compound of formula (I) from primary alcohols is desired, the due aminoalkanol (II) or (II') is reacted with 1,1'-carbonyl-bis-(3-methylimidazolium)triflate, prepared in situ starting from carbonyldiimidazole and methyltriflate, or before the reaction, according to Saha, A. K., Schultz P. and Rapoport H., JACS, 111, 4856–4859 (1989). This reactant is used in a molar ratio of 1:2 moles of alkanol. Alternatively, the aminoalkanol is first activated with an alkali metal hydride or a strong organic base, e.g., butyl-lithium, then it is reacted with carbonyldiimidazole, always in a molar ratio of 2:1. In any case, the reaction occurs in mixture of solvents selected from the group consisting of nitromethane, tetrahydrofuran, dioxane, polyhalogenated solvents and the like, at a temperature ranging between about 0° C. and about 50° C., for from about 2 to about 24 hours.

Eventually, when a carbonate of formula (I) which is asymmetric is desired, it takes to prepare an imidazolide of formula (III) or (III'):

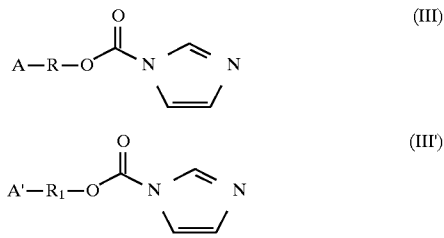

wherein A, A', R and $R_1$ are as defined above, by treating an aminoalkanol (II) or (II'), dissolved in an inert solvent such as tetrahydrofuran, dioxane, polyhalogenated solvents, etc., with carbonyldiimidazole at a temperature ranging between about 0° C. and about 80° C. for from about 1 to about 8 hours. The compound (III) or (III') is then reacted with another aminoalkanol (II') or (II) in an inert solvent such as polyhalogenated solvents, tetrahydrofuran, dioxane, etc., in the presence either of catalytic amounts of metallic sodium or of an equipollent strong base, e.g. butyl-lithium, sodium hydride, LDA (lithium diisopropyl-amide), at a temperature ranging between about 0° C. and about 50° C. for from 1 to 24 hours.

The latter procedure is also advantageously used for obtaining a symmetric carbonate of formula (I) from not primary alcohols.

The compounds of formula (I') are prepared by salifying compounds of formula (I) with a suitable pharmaceutically acceptable acid. Such salification is effected according to procedures known to the skilled in the art, by treating the carbonate of formula (I) with the due acid in at least equimolar ratios, depending on the desired salification degree.

As for the compounds of formula (I), the $^1$H-NMR spectra were effected in deuterate chloroform ($CDCl_3$), by a VARIAN GEMINI 200 spectrometer, and the $^{13}$C-NMR spectra were effected using a VARIAN GEMINI 200 spectrometer and considering the $CDCl_3$ 77.0 p.p.m peak as reference.

As for the compounds of formula (I'), the $^1$H-NMR spectra were effected in deuterate water ($D_2O$) by a VARIAN GEMINI 200 spectrometer, and the $^{13}$C-NMR spectra were effected by a VARIAN GEMINI 200 spectrometer and considering the TSP [sodium 3-(trimethylsilyl)-propane sulfonate] 0.0 p.p.m peak as reference.

EXAMPLE 1

Di-(N-butyl-4-piperidyl)methyl carbonate dihydrochloride

A] Thionyl chloride (55.27 g, 0.46 mole) was slowly dropped into 300 ml of absolute methanol at 0° C. The reaction mixture was stirred for 15 minutes at such temperature, then slowly added with piperidin-4-carboxyl acid (30 g, 0.23 mole), and heated to 50° C. for 1 hour, stirred overnight at room temperature, then evaporated to dryness, while taking up more times in absolute ethanol, and gave 43 g (quantitative yield) of crude piperidin-4-carboxyl acid methyl ester hydrochloride which was used as such in the following step.

B] The compound under A] (4.3 g, 0.23 mole) was dissolved in a 0.1M solution of sodium hydroxide and extracted with dichloromethane. The organic phase was anhydrified over sodium sulfate, then evaporated thus obtaining 27.6 g (0.193 mole) of free base which was dissolved in 100 ml of tetrahydrofuran (THF) and slowly dropped, at 0° C. under argo, into a lithium-aluminiun hydride suspension (11.1 g, 0.289 mole) in 150 ml of THF. The reaction mixture was stirred overnight at room temperature, then slowly added dropwise with a mixture of 48 ml of THF and 54 ml of water at 0° C., followed by a 30% solution of sodium hydroxide (11 ml) and water (66 ml). The resultant solid was filtrated off and the filtrate evaporated to dryness providing 19.9 g (yield: 88%) of 4-hydroxymethyl-piperidine which was used as such in the following step.

C] A solution of the compound under B] (19.8 g, 0.172 mole) and triethylamine (24 ml, 0.172 mole) in 200 ml of methanol, was added dropwise with 22.2 ml (0.2 mole) of butyl-bromide. The mixture was refluxed for 6 hours, then evaporated to dryness. The crude was dissolved in 100 ml of 1N HCl and washed with ethyl ether. The aqueous phase was brought to basic pH by 32% sodium hydroxide, then extracted with ethyl ether. The organic phase was anhydrified over sodium sulfate and evaporated. The crude was purified by distillation under vacuum and yielded 19.2 g of N-butyl-4-hydroxymethyl-piperidine (b.p.—96°–97° C./1 mmHg) (yield: 65%).

| Elemental analysis: | C | H | N |
|---|---|---|---|
| calculated | 70.12 | 12.36 | 8.18 |
| found | 70.05 | 12.53 | 8.19 |
| $^1$H-NMR: | d (2H) 3.44; m (2H) 2.93; m (2H) 2.28; m (2H) 1.88; m (2H) 1.72; m (7H) 1.54 ÷ 1.15; t (3H) 0.89. | | |
| $^{13}$C-NMR: | 67.82; 59.10; 53.75 (2C); 30.80; 29.28; 28.97 (2C); 21.07; 14.21. | | |

D] A solution of the compound under C] (13.7 g, 79.9 mmoles) in 130 ml of dichloromethane was added with metallic sodium (184 mg, 7.9 mmoles) in small pieces. The mixture was stirred for 1 hour at room temperature under argo, then slowly added with carbonyldiimidazole (CDI) (5.82 g, 35.9 mmoles) in dichloromethane (60 ml). The mixture was left under stirring overnight at room temperature, and the organic phase was washed with 200 ml of water, then with 0.025N HCl (4×250 ml). The organic phase was anhydrified over sodium sulfate and evaporated to dryness, and the resultant residue was dissolved in hexane, filtrated and evaporated again thus yielding 9.5 g (yield: 71%) of di-(N-butyl-4-piperidyl) methyl carbonate as a colourless oil.

| Elemental analysis: | C | H | N |
|---|---|---|---|
| calculated | 68.44 | 10.94 | 7.60 |
| found | 68.91 | 10.98 | 7.73 |
| $^1$H-NMR: | d (4H) 3.97; m (4H) 2.93; m (4H) 2.30; m (4H) 1.89; m (18H) 1.79 ÷ 1.21; t (6H) 0.92. | | |
| $^{13}$C-NMR: | 155.54; 72.44; 58.98; 53.24 (2C); 35.56; 29.35; 28.91 (2C); 21.02; 14.20. | | |

E] 2N HCl in ethyl ether (1.5 ml, 3 mmoles) was added to a solution of the compound under D] (1.1 g, 3 mmoles) in 35 ml of chloroform, at 0° C. The reaction mixture was evaporated to dryness and taken up more times in fresh chloroform. There was thus obtained the title product as an oil.

| Elemental Analysis: | C | H | N | Cl |
|---|---|---|---|---|
| calculated | 58.27 | 9.33 | 6.18 | 15.64 |
| found | 57.19 | 9.77 | 6.30 | 15.61 |
| $^1$H-NMR: | d (4H) 4.05; m (4H) 3.57; m (4H) 3.05; m (4H) 2.92; m (6H) 1.99; m (8H) 1.78 ÷ 1.42; m (4H) 1.32; t (6H) 0.88. | | | |
| $^{13}$C-NMR: | 158.51; 74.15 (2C); 59.86 (2C); 55.06 (4C); 35.47 (2C); 28.55 (4C); 28.37 (2C); 22.16 (2C); 15.63 (2C). | | | |

EXAMPLE 2

Di-4-(N,N-dibutylamino)cyclohexyl carbonate dihydrochloride

A] Trans-4-aminocyclohexanol hydrochloride (67 g, 0.44 mole) was dissolved into a 20% solution of sodium hydroxide, and extracted with chloroform. The organic phase was anhydrified over sodium sulfate and evaporated to give 48.3 g of free base which was dissolved in 400 ml of dioxane and 100 ml of ethanol. This solution was added with butylbromide (233 ml, 2.15 moles) and a 20% solution of sodium hydroxide (87 ml, 0.43 mole). The reaction mixture was heated for 1 hour, then added with further 20% sodium hydroxide (87 ml, 0.43 mole) and refluxed for 48 hours. The solution was cooled, the phases separated and the organic one evaporated to dryness. The resultant crude was taken up in 300 ml of water and 50 ml of 37% HCl. The aqueous phase was then washed with chloroform (2×150 ml), brought to basic pH with 60 ml of 32% sodium hydroxide, and extracted with ethyl ether (2×250 ml). The organic phase was washed with 0.03N HCl (3×120 ml), anhydrified over sodium sulfate and evaporated to give 83 g of a crude which, by distillation under vacuum, provided 74.5 g of 4-(N,N-dibutylamino) cyclohexanol (b.p.—134°–137° C./1 mmHg) (yield: 74%).

| Elemental analysis: | C | H | N |
|---|---|---|---|
| calculated | 73.95 | 12.85 | 6.16 |
| found | 73.77 | 12.91 | 6.14 |
| $^1$H-NMR: | m (1H) 3.55; m (1H) 2.46; m (4H) 2.39; m (2H) 2.05 ÷ 1.95; m (2H) 1.83 ÷ 1.69; m (12H) 1.46 ÷ 1.17; t (6H) 0.90. | | |
| $^{13}$C-NMR: | 71.06; 59.24; 50.74 (2C); 35.22 (2C); 31.47 (2C); 26.66 (2C); 20.82 (2C); 14.27 (2C). | | |

B] A solution of CDI (19.7 g, 65.9 mmoles) in 100 ml of nitromethane was slowly added with methyltriflate (14.5 ml, 130 mmoles) at 0° C. under argo. The mixture was stirred for 15 minutes at room temperature, then slowly poured into a solution of the compound under A] (30 g, 130 mmoles) in 300 ml of THF. Such mixture was stirred for 24 hours at room temperature, then evaporated to small volume, taken up in chloroform, and the organic phase was washed with water (4×200 ml), 0.03M HCl (4×100 ml), anhydrified over sodium sulfate and evaporated. The crude was purified by chromatography on a silica gel column (230–400 mesh) by eluting with hexane-ethyl acetate 1:1. There were thus obtained 9.5 g of di-4-(N,N-dibutylamino)cyclohexyl carbonate as a colourless oil (yield: 30%).

| Elemental analysis: | C | H | N |
|---|---|---|---|
| calculated | 72.45 | 11.74 | 5.83 |
| found | 72.22 | 11.78 | 5.72 |

| $^1$H-NMR: | m (2H) 4.47; m (2H) 2.48; m (8H) 2.39; m (4H) 2.17 ÷ 2.04; m (4H) 1.87 ÷ 1.72; m (24H) 1.51 ÷ 1.19; t (12H) 0.89. |
|---|---|
| $^{13}$C-NMR: | 154.26; 76.79 (2C); 58.92 (2C); 50.70 (4C); 31.50 (2C); 31.19 (4C); 26.42 (4C); 20.77 (4C); 14.25 (4C). |

C] Following the procedure of Example 1,E], and using the compound under B] (1.44 g, 3 mmoles), there was obtained a crude which, taken up in ethyl ether, filtrated and dried under vacuum provided the title product (m.p.—251°–252° C.).

| Elemental Analysis: | C | H | N | Cl |
|---|---|---|---|---|
| calculated | 62.91 | 10.56 | 5.06 | 12.81 |
| found | 60.16 | 10.32 | 4.78 | 14.94 |

| $^1$H-NMR: | m (2H) 4.53; m (2H) 3.34; m (8H) 3.11; m (8H) 2.13; m (24H) 1.76 ÷ 1.24; t (12H) 0.89. |
|---|---|
| $^{13}$C-NMR: | 157.13; 78.58 (2C); 63.77 (2C); 53.87 (4C); 31.58 (4C); 29.39 (4C); 26.76 (4C); 15.69 (4C). |

EXAMPLE 3

Di-[trans-2-(N,N-dibutylamino)]-cyclohexyl carbonate dihydrochloride

A] A solution of 43 ml (0.25 mole) of dibutylamine in 770 ml of dichloromethane was added with a 0.91M solution of 280 ml (0.025 mole) of triethyl-aluminium in hexane, at 0° C. under argo, and the resultant reaction mixture was stirred for 30 minutes at room temperature, then dropwise added with 25.8 ml (0.25 mole) of 7-oxabicyclo[4.1.0] heptane, and stirred overnight. A 6M solution of 200 ml (1.2 moles) of sodium hydroxide was added very slowly, and the mixture was stirred for 2 hours at room temperature. The phases were separated, and the organic one was washed with water (2×50 ml), anhydrified over sodium sulfate and evaporated. The resultant crude was distilled under vacuum to provide 43.7 g (yield: 75%) of trans-2-(N,N-dibutylamino)-cyclohexanol (b.p.—105°–107° C./1 mmHg).

| Elemental analysis: | C | H | N |
|---|---|---|---|
| calculated | 73.95 | 12.85 | 6.16 |
| found | 74.08 | 12.93 | 6.13 |

| $^1$H-NMR: | m (12H) 3.30; m (5H) 2.60 ÷ 2.06; m (4H) 1.81 ÷ 1.60; m (12H) 1.50 ÷ 1.12; t (6H) 0.91. |
|---|---|
| $^{13}$C-NMR: | 69.35; 66.87; 49.85 (2C); 33.38; 31.63 (2C); 25.90; 24.36; 22.62; 20.68 (2C); 14.15 (2C). |

B] Starting from CDI (12.3 g, 75.8 mmoles), methyltriflate (16.7 ml, 150 mmoles) in 100 ml di nitromethane, and the compound under A] (34.5 mg, 150 mmoles) in 300 ml of THF, and following the procedure of Example 2,B], there were obtained 13 g (yield: 36%) of di-trans-2-(N,N-dibutylamino)-cyclohexyl carbonate as a colourless oil.

| Elemental analysis: | C | H | N |
|---|---|---|---|
| calculated | 72.45 | 11.74 | 5.83 |
| found | 72.35 | 11.80 | 5.78 |

| $^1$H-NMR: | m (2H) 4.62; m (10H) 2.64 ÷ 2.27; m (2H) 2.14 ÷ 1.98; m (6H) 1.86 ÷ 1.60; m (24H) 1.45 ÷ 1.13; t (12H) 0.88. |
|---|---|
| $^{13}$C-NMR: | 154.83 (0.3C); 154.46 (0.7C); 77.29 (1.4C); 76.03 (0.6C); 63.55 (0.6C); 62.79 (1.4C); 51.01 (2.8C); 50.54 (1.2C); 32.19 (2.8C); 31.84 (1.2C); 28.16 (1.4C); 26.32 (0.6C); 25.53 (1.4C); 24.59 (0.6C); 24.48 (1.4C); 22.78 (0.6C); 20.64 (2.8C); 20.58 (1.2C); 14.34 (4C). |

C] Following the procedure of Example 1,E] and using the compound under B] (1.44 g, 3 mmoles), there was obtained a crude which was taken up in ethyl ether, filtrated and dried under vacuum to provide the title product (m.p.—172°–175° C.).

| Elemental Analysis: | C | H | N | Cl |
|---|---|---|---|---|
| calculated | 62.91 | 10.56 | 5.06 | 12.81 |
| found | 60.64 | 10.41 | 4.80 | 13.95 |

| $^1$H-NMR: | m (2H) 4.95; m (2H) 3.59; m (8H) 3.37 ÷ 2.89; m (4H) 2.30 ÷ 2.04; m (28H) 1.86 ÷ 1.23; m (12H) 0.89. |
|---|---|
| $^{13}$C-NMR: | 155.99; 78.34 (0.7C); 78.12 (1.3C); 66.50 (1.3C); 66.31 (0.7C); 55.55 (0.7C); 55.16 (1.3C); 53.62 (0.7C); 53.32 (1.3C); 33.33 (2C); 29.92 (0.7C); 29.81 (1.3C); 29.19 (1.3C); 29.06 (0.7C); 26.02 (2C); 25.53 (2C); 25.34 (0.7C); 25.24 (1.3C); 22.41 (2.6C); 22.36 (1.4C); 15.71 (1.4C); 15.66 (2.6C). |

EXAMPLE 4

[(3-Pyridyl)methyl]-[trans-2'-(N,N-dibutylamino) cyclohexyl] carbonate dihydrochloride A] A solution of the compound of Example 3,A] (21 g, 92 mmoles) in 200 ml of dichloromethane was dropwise added with CDI (16.5 g, 101 mmoles) in dichloromethane (160 ml). The mixture was stirred for 4 hours at room temperature, then refluxed for 2 hours. The organic phase was washed with water (2×100 ml), anhydrified over sodium sulfate and evaporated to give 27 g (yield: 93%) of imidazolyl-[trans-2-(N,N-dibutylamino)cyclohexyl] formate.

$^1$H-NMR: s (1H) 8.13; s (1H) 7.42; s (1H) 7.06; m (1H) 4.96; m (1) 2.60; m (5H) 2.51–2.12; m (3H) 1.96–1.73; m (12H) 1.60–1.08; t (6H) 0.82.

B] A solution of 3-hydroxymethyl-pyridine (4.8 g, 44 mmoles) in 50 ml of dichloromethane was added with metallic sodium (200 mg, 8 mmoles) in small pieces. The mixture was stirred for 1 hour at room temperature, then dropwise added with a solution of the compound under A] (13.5 g, 42 mmoles) in 60 ml of dichloromethane. The solution was stirred overnight, and the organic phase washed with water (2×50 ml), anhydrified over sodium sulfate and the solvent evaporated. The resultant crude was dissolved in hexane, and the solution was washed with 0.05M HCl (3×70 ml), anhydrified over sodium sulfate and evaporated to dryness thus giving 11 g (yield: 72%) of [(3-pyridyl)methyl]-[trans-2'-(N,N-dibutylamino)cyclohexyl] carbonate.

| Elemental analysis: | C | H | N |
|---|---|---|---|
| calculated | 69.58 | 9.45 | 7.73 |
| found | 69.37 | 9.51 | 7.77 |

| | |
|---|---|
| $^1$H-NMR: | s (1H) 8.64; dd (1H) 8.58; dt (1H) 7.73; dd (1H) 7.29; m (2H) 5.15; m (1H) 4.64; m (5H) 2.55 ÷ 2.22; m (4H) 2.12 ÷ 1.68; m (12H) 1.48 ÷ 1.10; m (6H) 0.85. |
| $^{13}$C-NMR: | 154.81; 149.84 (2C); 136.14; 131.52; 123.48; 77.03; 66.58; 63.63; 50.21 (2C); 32.06; 31.64 (2C); 25.34; 25.08; 24.58; 20.57 (2C); 14.32 (2C). |

C] Following the procedure of Example 1,E] and using the compound under B] (1.3 g, 3 mmoles), there was obtained the title product as an oil.

| Elemental Analysis: | C | H | N | Cl |
|---|---|---|---|---|
| calculated | 57.93 | 8.33 | 6.43 | 16.28 |
| found | 57.55 | 8.19 | 6.25 | 16.05 |

| | |
|---|---|
| $^1$H-NMR: | d (1H) 8.87; dd (1H) 8.76; dt (1H) 8.64; dd (1H) 8.07; m (2H) 5.41; m (1H) 4.95; m (1H) 3.55; m (3H) 3.32 ÷ 3.50; m (1H) 2.92; m (2H) 2.46; m (14H) 1.84 ÷ 1.15; t (3H) 0.87; t (3H) 0.80. |
| $^{13}$C-NMR: | 156.64; 149.24; 144.28; 143.72; 138.30; 130.28; 78.18; 68.64; 66.17; 55.16; 53.43; 33.37; 29.66; 29.03; 26.00; 25.53; 25.19; 22.30 (2C); 25.56; 15.63 (2C). |

EXAMPLE 5

[(N-Methyl-3-piperidyl)methyl]-[trans-2'-(N,N-dibutylamino)cyclohexyl] carbonate hydrochloride hydrate A] At 0° C., 3-hydroxymethyl-piperidine (20 g, 173 mmoles) was slowly added to formic acid (63 ml, 1.66 moles) then a 40% solution of formaldehyde was added (62.4 ml, 833 mmoles). The mixture was refluxed for 5 hours, then the solvent was evaporated and the residue taken up in little water, brought to basic pH with 32% sodium hydroxide and extracted with ethyl ether. The organic phase was anhydrified over sodium sulfate and evaporated. The resultant crude was purified by distillation and provided 17 g (yield: 76%) of N-methyl-3-hydroxymethylpiperidine (b.p.—85°–86° C./1 mmHg).

| Elemental analysis: | C | H | N |
|---|---|---|---|
| calculated | 65.07 | 11.70 | 10.84 |
| found | 64.75 | 11.85 | 10.84 |

| | |
|---|---|
| $^1$H-NMR: | m (2H) 3.5; m (1H) 2.83; m (1H) 2.66; s (3H) 2.23; m (6H) 2.05 ÷ 1.45; m (1H) 1.00. |
| $^{13}$C-NMR: | 66.69; 59.59; 56.43; 46.83; 38.67; 27.02; 24.90. |

B] The product was prepared starting from the compound under A] (5.7 g, 44 mmoles), from the one prepared in Example 4,A] (13.5 g, 42 mmoles) and metallic sodium (198 mg, 8.6 mmoles) in 170 ml of dichloromethane, following the procedure of Example 4,B]. The crude was purified by chromatography on a silica gel column (230–400 mesh; eluent: hexane/ethyl acetate 3:7) to give 7.06 g (yield: 44%) of [(N-methyl-3-piperidyl)-methyl]-[trans-2'-(N,N-dibutyl-amino)cyclohexyl] carbonate as a colourless oil.

| Elemental analysis: | C | H | N |
|---|---|---|---|
| calculated | 69.07 | 11.06 | 7.32 |
| found | 69.20 | 11.20 | 7.37 |

| | |
|---|---|
| $^1$H-NMR: | m (1H) 4.61; m (2H) 3.97; m (1H) 2.86; m (1H) 2.74; m (4H) 2.55 ÷ 2.27; s (3H) 2.25; m (18H) 2.12 ÷ 0.97; t (6H) 0.88. |
| $^{13}$C-NMR: | 155.12; 76.51; 70.40; 63.57; 59.16 (0.5C); 59.00 (0.5C); 56.26; 50.29 (2C); 46.83; 36.13; 32.12; 31.78 (2C); 26.73 (0.5C); 26.65 (0.5C); 25.39 (2C); 24.95; 24.61; 20.57 (2C); 14.38 (2C). |

C] Following the procedure of Example 1,E] and using the compound under B] (1.15 g, 3 mmoles), the title product was obtained as an oil.

| Elemental analysis: | C | H | N | Cl |
|---|---|---|---|---|
| calculated | 55.80 | 9.79 | 5.92 | 14.97 |
| found | 54.73 | 9.96 | 5.57 | 14.89 |

| | |
|---|---|
| $^1$H-NMR: | m (1H) 4.93; m (2H) 4.13; m (8H) 3.62 ÷ 2.69; s (3H) 2.83; m (21H) 2.30 ÷ 1.23; t (6H) 0.89. |
| $^{13}$C-NMR: | 157.08; 77.70; 72.44; 66.35; 58.81; 57.44; 55.04; 54.19; 46.46; 36.86; 33.46; 29.45; 26.36; 26.07; 25.56; 25.28 (2C); 25.17; 22.35; 15.67. |

EXAMPLE 6

Di-5-(N-benzyl-N-hexylamino)-2-pentyl carbonate

A] 200 ml (1.49 moles) of hexylamine cooled to 5° C. were added with benzyl bromide (42.3 ml, 0.35 mole), and the resultant mixture was stirred for 1 hour at room temperature. The hexylamine in excess was then distilled off under vacuum, and the residue dissolved in 300 ml of ethyl ether and washed with 200 ml of 0.5N sodium hydroxide. The ether phase was anhydrified over sodium sulfate and evaporated to dryness thus yielding 75.5 g of a crude which, by distillation under vacuum, gave 59 g (yield: 89%) of N-benzyl-N-hexylamine (b.p.—90°–95° C./0.6 mmHg).

B] A solution of levulinic acid (71 g, 0.61 mole) in 700 ml of acetone was added with triethylamine (83.47 ml, 0.61 mole), and the mixture was stirred for 15 minutes at room temperature, then cooled to 5° C., and added with a solution of isobutyl chloroformate (79.9 ml, 0.61 mole) in 300 ml of acetone, while stirring for 15 minutes at the same temperature. The solid was filtered off and the mother liquor was added to a solution of the compound under A] (117 g, 0.61 mole) in 400 ml of acetone. The mixture was stirred overnight at room temperature, then evaporated to dryness, and the residue dissolved in 500 ml of ethyl ether, washed first with 200 ml of 0.5N hydrochlorid acid, then with 200 ml of a 0.5N solution of sodium hydroxide, and lastly with 200 ml of water. The ether phase was anhydrified over sodium sulfate and evaporated to dryness to give 167 g (yield: 95%) of crude N-benzyl-N-hexyl-2-oxo-pentanamide which was used as such in the next step.

C] A suspension of lithium aluminium hydride (43.5 g, 1.14 moles) in 2 l of THF, cooled to 0° C., was added with a solution of the compound under B] (167 g, 0.57 mole) dissolved in 830 ml of THF. At the end of the addition, the reaction mixture was stirred overnight at room temperature, then dropwise slowly added with a mixture of THF (118 ml) and water (13 ml) at 0° C., followed by a 20% solution of sodium hydroxide (40 ml) and water (163 ml). The resultant solid was filtered off and the filtrate evaporated to dryness thus yielding 142.6 g of a crude which, by distillation under vacuum, provided 93.3 g (yield: 58%) of 5-(N-benzyl-N-hexylamino)-2-pentanol (b.p.—147°–151° C./0.5 mmHg).

| Elemental analysis: | C | H | N |
|---|---|---|---|
| calculated | 77.92 | 11.26 | 5.05 |
| found | 78.19 | 11.29 | 5.07 |
| $^1$H-NMR: | m (5H) 7.34 ÷ 7.20; m (1H) 3.73; m (2H) 3.59; m (4H) 2.55 ÷ 2.18; m (12H) 1.74 ÷ 1.15; m (3H) 0.86. | | |
| $^{13}$C-NMR: | 138.13; 129.58 (2C); 128.42 (2C); 127.23; 67.61; 58.46; 54.74; 53.52; 39.02; 31.82; 27.33; 25.79; 24.59; 23.86; 22.76; 14.18. | | |

D] A solution of the compound under C] (40 g, 0.14 mole) dissolved in 200 ml of THF, was added with a solution of 1,1'-carbonyl-bis-(3-methylimidazole)-triflate (0.072 moles) in 200 ml of THF, cooled to 5° C. The resultant solution was stirred overnight at room temperature, then evaporated to dryness, and the residue taken up in 300 ml of chloroform and washed with a 0.5N solution of sodium hydroxide (2×100 ml). The organic phase was anhydrified over sodium sulfate and evaporated to dryness to yield 32 g of a crude which by silica-gel chromatography (230–400 mesh; eluent: hexane-ethyl acetate 8:2), provided 17 g (yield: 40%) of the title product.

| Elemental analysis: | C | H | N |
|---|---|---|---|
| calculated | 76.50 | 10.41 | 4.82 |
| found | 76.63 | 10.49 | 4.82 |
| $^1$H-NMR: | m (10H) 7.32 ÷ 7.20; m (2H) 4.72; s (4H) 3.53; m (8H) 2.43; m (24H) 1.65 ÷ 1.20; d (6H) 1.25; m (6H) 0.87. | | |
| $^{13}$C-NMR: | 154.72; 140.30 (2C); 128.92 (4C); 128.22 (4C); 126.78 (2C); 75.03 (2C); 58.77 (2C); 53.96 (2C); 53.58 (2C); 33.86 (2C); 31.95 (2C); 27.26 (2C); 27.12 (2C); 23.12 (2C); 22.83 (2C); 20.12 (2C); 14.24 (2C). | | |

EXAMPLE 7

Di-5-(N-methyl-N-hexylamino)-2-pentyl carbonate

A] The compound of Example 6,C] (35.38 g, 0.128 mole) was hydrogenated at 15 psi in 155 ml of methanol and 155 ml of 1N HCl in the presence of 3.5 g of 10% Pd/C. When the hydrogen absorption ceased, the exhausted catalyzer was filtered off, the methanol was evaporated and the resultant acid aqueous solution was washed with dichloromethane. The acid solution was alkalinized with 32% sodium hydroxide and the crude was extracted with ethyl ether (3×70 ml). The ether phase was dried over sodium sulfate and evaporated to dryness to give 20.5 g (yield: 85%) of crude 5-(N-hexylamino)-2-pentanol which was used as such in the next step.

B] Benzyl chloroformate (22.69 g, 0.133 mole) in 30 ml of ether was added to a solution of the compound under A] (22.7 g, 0.121 mole), triethylamine (18.5 ml, 0.133 mole) in 200 ml of ethyl ether and 30 ml of dichloromethane, cooled to 0° C. At the end of the addition, the reaction mixture was stirred overnight at room temperature. The formed solid was filtered off and the mother liquor was washed with 100 ml of 1N HCl, anhydrified over sodium sulfate and evaporated to dryness under vacuum to give 36.35 g (yield: 93%) of 5-(N-hexyl-N-carbobenzyloxy) amino-2-pentanol, which was used as such in the following step.

C] A suspension of lithium aluminium hydride (6.44 g, 0.17 mole) in 185 ml of THF, was cooled to 0° C. and dropwise added with the compound under B] (36.35 g, 0.133 mole) dissolved in 300 ml of THF. At the end of the addition, the reaction mixture was stirred overnight at room temperature, then slowly dropwise added with a mixture of THF (18.19 ml) and water (2.18 ml) at 0° C., followed by a 20% solution of sodium hydroxide (6.5 ml) and water (25.9 ml). The resultant solid was filtered off and the filtrate evaporated to dryness under vacuum. The residue was taken up in 500 ml of ethyl ether and extracted with 10% HCl (2×200 ml). The acid aqueous solution was then washed with ethyl ether (2×150 ml), alkalinized with 32% sodium hydroxide and extracted with dichloromethane (3×100 ml). The combined organic phases were anhydrified over sodium sulfate and evaporated to dryness to give 19.62 g of a crude, which by distillation under vacuum provided 17.2 g (yield: 75%) of 5-(N-methyl-N-hexylamino)-2-pentanol (b.p.=102°–104° C./1 mmHg).

| Elemental analysis: | C | H | N |
|---|---|---|---|
| calculated | 71.58 | 13.52 | 6.96 |
| found | 70.92 | 13.40 | 6.87 |
| $^1$H-NMR: | m (1H) 3.68; m (4H) 2.41 ÷ 2.25; s (3H) 2.20; m (12H) 1.69 ÷ 1.23; d (3H) 1.14; m (3H) 0.86. | | |
| $^{13}$C-NMR: | 67.53; 58.70; 58.23; 41.29; 39.65; 31.86; 27.33; 26.88; 25.23; 23.93; 22.71; 14.18. | | |

D] A solution of the compound under C] (11.7 g, 0.058 mole) in 50 ml of THF, was added to a solution of 1,1'-carbonyl-bis-(3-methylimidazole)triflate (0.029 mole) according to the procedure described in Example 6,C]. The mixture was heated to 45° C. for 8 hours, then evaporated to dryness, and the residue was taken up in ethyl ether (100 ml). The ether solution weds washed with 0.05N HCl (6×30 ml), anhydrified over sodium sulfate and evaporate to dryness thus yielding 7 g of a crude which was extracted with hexane (3×100 ml) and gave 4.4 g (yield: 35%) of the title product.

| Elemental analysis: | C | H | N |
|---|---|---|---|
| calculated | 70.04 | 12.23 | 6.53 |
| found | 70.56 | 12.40 | 6.67 |

| | |
|---|---|
| $^1$H-NMR: | m (2H) 4.76; m (8H) 2.34 ÷ 2.25; s (6H) 2.18; m (24H) 1.73 ÷ 1.20; d (6H) 1.27; m (6H) 0.89. |
| $^{13}$C-NMR: | 154.70; 74.96 (2C); 58.09 (2C); 57.59 (2C); 42.39 (2C); 33.96 (2C); 31.99 (2C); 27.47 (2C); 27.42 (2C); 23.33 (2C); 22.79 (2C); 20.11 (2C); 14.22 (2C). |

EXAMPLE 8

Di-4-(N,N-dibutylamino)-2-butyl carbonate dihydrochloride

A] A mixture of ethyl acetoacetate (50 g, 0.38 mole) and dibutylamine (49.65 g, 0.38 mole) was heated to 150° C. for one day. After cooling, the reaction mixture was taken up in 500 ml of ethyl ether and washed with 200 ml of 1N HCl and 200 ml of water. The ether phase was anhydrified over sodium sulfate, and evaporated to dryness thus yielding 86.7 g of a crude which was distilled under vacuum to give 54.86 g (yield: 67%) of N,N-dibutyl-3-oxo-butanamide.

B] A slurry of lithium aluminium hydride (14.16 g, 0.37 moli) in 500 ml of THF, cooled to 0° C., was dropwise added with a solution of the compound under A] (60 g, 0.28 mole) in 200 ml of THF. After the addition, the mixture was stirred overnight at room temperature, then slowly dropwise added with a mixture of THF (48 ml) and water (7 ml) at 0° C., followed by a 20% solution of sodium hydroxide (16 ml) and water (68 ml). The formed solid was filtered off and the filtrate evaporated to dryness under vacuum, thus giving 51 g of a crude which distilled under vacuum gave 41 g (yield: 73%) of 4-(N,N-dibutylamino)-2-butanol (b.p.—90°–92° C./1 mmHg).

| Elemental analysis: | C | H | N |
|---|---|---|---|
| calculated | 71.58 | 13.52 | 6.96 |
| found | 71.04 | 13.56 | 6.89 |

| | |
|---|---|
| $^1$H-NMR: | m (1H) 3.93; m (6H) 2.78 ÷ 2.15; m (10H) 1.68 ÷ 1.19; d (3H) 1.15; t (6H) 0.91. |
| $^{13}$C-NMR: | 70.03; 54.48; 53.94 (2C); 34.17; 29.08 (2C); 23.68; 20.82 (2C); 14.20 (2C). |

C] A solution of the compound under B] (21.77 g, 0.11 mole) in 200 ml of anhydrous THF, was added to a solution of 1,1'-carbonyl-bis-(3-methyl-imidazole)triflate (0.05 mole) in 80 ml of nitromethane, as described in Example 6,C]. The mixture was stirred overnight at room temperature and evaporated to small volume, and the residue taken up in ethyl ether (100 ml). The ether solution was washed with 0.5N sodium hydroxide (2×25 ml) and 0.05N HCl (4×30 ml). The organic phase was anhydrified over sodium sulfate, then evaporated to dryness yielding 8.5 g of a crude which, by chromatography on a silica gel column (230–400 mesh; eluent: hexane/ethyl acetate 1:1) provided 6.5 g (yield: 28%) of di-4-(N,N-dibutylamino)-2-butyl carbonate.

| Elemental analysis: | C | H | N |
|---|---|---|---|
| calculated | 70.04 | 12.23 | 6.53 |
| found | 70.62 | 12.54 | 6.60 |

| | |
|---|---|
| $^1$H-NMR: | m (2H) 4.80; m (12H) 2.50 ÷ 2.33; m (20H) 1.3 ÷ 1.17; d (6H) 1.29; t (12H) 0.90. |
| $^{13}$C-NMR: | 154.48; 73.89 (1.3C); 73.75 (0.7C); 54 (4C); 50.19 (1.3C); 50.10 (0.7C); 33.63 (2C); 29.45 (4C); 20.86 (4C); 20.29 (2C); 14.24 (4C). |

D] Following the procedure of Example 1,E] and using the compound under C] (1.5 g, 3 mmoles), the title product was obtained as an oil.

| Elemental analysis: | C | H | N | Cl |
|---|---|---|---|---|
| calculated | 59.86 | 10.85 | 5.58 | 14.14 |
| found | 57.28 | 10.86 | 5.22 | 14.43 |

| | |
|---|---|
| $^1$H-NMR: | m (2H) 4.79; m (4H) 3.19; m (8H) 3.10; m (4H) 2.00; m (8H) 1.61; m (8H) 1.33; d (6H) 1.27; t (12H) 0.87. |
| $^{13}$C-NMR: | 157.08; 76.57 (2C); 55.99 (4C); 51.79 (2C); 31.96 (2C); 28.10 (2C); 28.04 (2C); 22.11 (4C); 21.68 (2C); 15.67 (4C). |

EXAMPLE 9

Di-4-(N,N-dibutylamino)-1-pentyl carbonate

A] A solution of 100 g (0.86 mole) of levulinic acid in 1 l of acetone was added with 118 ml (0.86 mole) of triethylamine, and stirred for 15 minutes at room temperature. The mixture was cooled to 5° C. and added with a solution of ethyl chloroformate (83.3 ml, 0.86 mole) in 500 ml of acetone, then stirred for 15 minutes. The solid was filtered off and the mother liquor was added to a solution of dibutylamine (180 ml, 1 mole) in 1 l of acetone, then stirred overnight at room temperature, evaporated to dryness under vacuum, and the residue was dissolved in 1 l of ethyl ether, washed with 400 ml of 0.5N HCl, then with 400 ml of 0.5N sodium hydroxide. The ether phase was anhydrified over sodium sulfate and evaporated to dryness thus providing 175.5 g of a crude which by distillation under vacuum gave 112.5 g (yield: 57%) of N,N-dibutyl-4-oxo-pentanamide (b.p. 135°–138° C./1 mmHg).

| Elemental analysis: | C | H | N |
|---|---|---|---|
| calculated | 68.68 | 11.08 | 6.16 |
| found | 68.75 | 11.17 | 6.08 |

B] A solution of the compound under A] (112.5 g, 0.49 mole) in 450 ml of methanol, cooled to 0° C., was added with small portions of sodium borohydride (20.5 g, 0.54 mole), while stirring at room temperature for 1 hour. The mixture was cooled again to 0° C., added with 25 ml of 37% HCl, then evaporated to small volume. The residue was taken up in 400 ml of acetone, the solid filtered off and the mother liquor evaporated to dryness yielding 116 g of crude N,N-dibutyl-4-hydroxy-pentanamide which was used as such in the following step.

C] Thionyl chloride (43 ml, 0.59 mole) was dropped into a solution of the compound under B] (116 g, 0.5 mole) in 1 l of chloroform, in the presence of pyridine (0.87 ml).

The reaction mixture was refluxed for 4 hours, then the solvent was evaporated under vacuum, and the residue dissolved in ethyl ether (500 ml) was washed with 200 ml of water and 200 ml of a 5% solution of sodium hydrocarbonate. The organic phase was anhydrified over sodium sulfate and evaporated to dryness under vacuum yielding 107.7 g (yield: 87%) of crude N,N-dibutyl-4-chloro-pentanamide which was used as such in the following step.

D] The compound under C] (30 g, 0.12 mole) and dibutylamine (86.3 g, 0.48 mole) were refluxed for 2 days. The mixture was the taken up in ethyl ether and, after filtering off the dibutylamine hydrochloride, evaporated to dryness while stripping the ethyl ether and the dibutylamine in excess, thus obtaining 38 g (yield: 93%) of crude N,N-dibutyl-4-dibutylamino-pentanamide which was used as such in the following step.

D] The compound under C] (30 g, 0.12 mole) and dibutylamine (86.3 g, 0.48 mole) were refluxed for 2 days. The mixture was the taken up in ethyl ether and, after filtering off the dibutylamine hydrochloride, evaporated to dryness while stripping the ethyl ether and the dibutylamine in excess, thus obtaining 38 g (yield: 93%) of crude N,N-dibutyl-4-dibutylamino-entanamide which was used as such in the following step.

E] A mixture of 38 g (0.166 mole) of the compound under D], 130 ml of concentrated sulforic acid and 100 ml of 37% HCl, was heated to 140°–150° C. for 3 days, then cooled in ice bath, neutralized with 50% sodium hydroxide, and extracted with ethyl acetate. The organic phase was anhydrified over sodium sulfate, and evaporated to dryness to give 22.65 g of 4-dibutylaminopentanoic acid which was used as such in the next step.

F] A suspension of 4.86 g (0.128 mole) of lithium aluminium hydride in 190 ml of THF, cooled to 0° C., was dropwise added with the compound under E] (22 g, 0.096 mole) in 66 ml of THF. At the end of the addition, the mixture was stirred overnight at room temperature, then slowly added dropwise with a mixture of THF (14.5 ml) and water (1.9 ml) at 0° C., followed by a 20% solution of sodium hydroxide (5 ml) and water (19 ml). The formed solid was filtered off and the filtrate evaporated to dryness under vacuum thus yielding 17 g of a crude which, by distillation under vacuum provided 12.7 g (yield: 63%) of 4-N-dibutylaminopentanol.

| Elemental analysis: | C | H | N |
|---|---|---|---|
| calculated | 72.50 | 13.57 | 6.50 |
| found | 72.60 | 13.64 | 6.60 |

| | |
|---|---|
| ¹H-NMR: | m (2H) 3.69 ÷ 3.39; m (1H) 2.77; m (2H) 2.61 ÷ 2.46; m (2H) 2.27 ÷ 2.12; m (12H) 1.86 ÷ 1.17; d (3H) 0.93; t (6H) 0.92. |
| ¹³C-NMR: | 63.05; 56.47; 50.23 (2C); 34.37; 30.45 (2C); 21.10 (2C); 14.18 (2C); 13.55. |

G] A solution of the compound under F] (8 g, 0.037 mole) dissolved in 20 ml of dichloromethane, was stirred for 1 hour at room temperature in the presence of 64 mg of sodium, then added with CDI (3 g, 0.018 mole) dissolved in 40 ml of THF. The resultant reaction mixture was stirred overnight at room temperature, then, after filtering off the remaining sodium, the solvent was evaporated to dryness. The residue was taken up in 100 ml of ethyl ether, then treated with water (3×30 ml) and 0.05N HCl (5×30 ml). The ether solution was anhydrified over sodium sulfate and evaporated under vacuum thus obtaining 4.6 g (yield: 54%) of the title product.

| Elemental analysis: | C | H | N |
|---|---|---|---|
| calculated | 71.00 | 12.36 | 6.13 |
| found | 70.90 | 12.43 | 6.19 |

| | |
|---|---|
| ¹H-NMR: | t (4H) 4.12; m (2H) 2.67; m (8H) 2.45 ÷ 2.17; m (24H) 1.88 ÷ 1.18; t (12H) 0.89; d (6H) 0.88. |
| ¹³C-NMR: | 155.61; 68.44 (2C); 54.54 (2C); 49.70 (4C); 31.68 (4C); 30.41 (2C); 26.43 (2C); 20.79 (4C); 14.29 (4C); 13.81 (2C). |

EXAMPLE 10

Di-5-(N,N-dibutylamino)-2-pentyl carbonate dihydrochloride hydrate

A] A 70% solution of sodium aluminium bis-(2-methoxyethoxy)dihydride (50 ml, 0.17 mole) in 100 ml of toluene, was added with a solution of the compound of Example 9,A] (17 g, 0.07 mole), in 30 ml of toluene and stirred for 30 minutes at room temperature. 40 ml of 1N sodium hydroxide were dropped therein after cooling the reaction mixture to 5° C. The organic phase was anhydrified and evaporated to dryness, and the residue was taken up in 100 ml of dichloromethane, then extracted with 0.5N HCl (2×50 ml). The acid aqueous solution was alkalinized with 3N sodium hydroxide and extracted with dichloromethane (3×50 ml). The organic phase was anhydrified over sodium sulfate and evaporated to dryness thus giving 9.6 g (yield: 60%) of 5-(N,N-dibutylamino)-2-pentanol.

| Elemental analysis: | C | H | N |
|---|---|---|---|
| calculated | 72.50 | 13.57 | 6.50 |
| found | 72.58 | 13.63 | 6.51 |

| | |
|---|---|
| ¹H-NMR: | m (1H) 3.65; m (6H) 2.56 ÷ 2.24; m (12H) 1.74 ÷ 1.15; d (3H) 1.11; t (6H) 0.87. |
| ¹³C-NMR: | 67.29; 54.95; 53.23 (2C); 39.36; 27.79 (2C); 24.81; 23.63; 20.65 (2C); 13.82 (2C). |

B] A solution of the compound under A] (9.6 g, 0.044 mole) in THF (17 ml) was dropped into a suspension of sodium hydride (0.66 g, 0.027 mole) in THF (17 ml). The sodium hydride in excess was filtered off and the mother liquor refluxed. CDI (3.9 g, 0.024 mole) in 45 ml of THF was added, the reaction mixture was stirred for 8 hours under reflux, cooled and added with 160 ml of water. The separated oil was taken up in 40 ml of hexane, washed with 0.07N HCl (3×20 ml) and water (2×20 ml). The organic phase was anhydrified over sodium sulfate and evaporated to dryness to provide 8 g (yield: 40%) of di-5-(N,N-dibutylamino)-2-pentyl carbonate.

| Elemental analysis: | C | H | N |
|---|---|---|---|
| calculated | 71.00 | 12.36 | 6.13 |
| found | 70.73 | 12.33 | 6.19 |

| | |
|---|---|
| ¹H-NMR: | m (2H) 4.73; m (12H) 2.39 ÷ 2.31; m (24H) 1.63 ÷ 1.16; d (6H) 1.24; t (12H) 0.87. |
| ¹³C-NMR: | 154.84; 74.88 (2C); 53.80 (6C); 33.75 (2C); 29.14 (4C); 22.87 (2C); 20.59 (4C); 19.83 (2C); 13.92 (4C). |

C] Following the procedure of Example 1,E] and using the compound under B] (1.4 g, 3 mmoles), the product in title was obtained as an oil.

| Elemental analysis: | C | H | N | Cl |
|---|---|---|---|---|
| calculated | 59.21 | 11.04 | 5.11 | 12.95 |
| found | 58.47 | 11.50 | 5.01 | 13.88 |

| | |
|---|---|
| $^1$H-NMR: | m (2H) 4.79; m (12H) 3.09; m (12H) 1.80 ÷ 1.54; m (8H) 1.33; d (6H) 1.25; t (12H) 0.88. |
| $^{13}$C-NMR: | 157.77 (0.5C); 157.68 (0.5C); 78.53; 78.47; 55.61 (4C); 55.06; 34.68 (2C); 28.09 (4C); 22.16 (4C); 22.06 (2C); 21.84; 21.67; 15.68 (4C). |

EXAMPLE 11

Di-5-(N-hexylamino)-2-pentyl carbonate dihydrochloride

A] The compound of Example 6 (11 g, 0.018 mole) was hydrogenated at 45 psi in 100 ml of THF, in the presence of 1.1 g of 10% Pd/C and trifluoroacetic acid (0.5 ml). The reaction mixture was shaked for 2 days, then the catalyzer was filtered off and the mother liquor evaporated to dryness. From the resultant crude (7 g) 4.5 g (yield: 62.5%) of di-5-(N-hexylamino)-2-pentyl carbonate were recovered by silica-gel chromatography (230–400 mesh; eluent: chloroform-methanol 7:3).

| Elemental analysis: | C | H | N |
|---|---|---|---|
| calculated | 68.95 | 12.08 | 6.99 |
| found | 68.59 | 12.12 | 6.80 |

| | |
|---|---|
| $^1$H-NMR: | m (2.H) 4.74; m (8H) 2.62 ÷ 2.53; m (26H) 1.75 ÷ 1.10; d (6H) 1.26; m (6H) 0.87. |
| $^{13}$C-NMR: | 154.67; 74.92 (2C); 50.23 (2C); 49.89 (2C); 33.84 (2C); 31.94 (2C); 30.29 (2C); 27.23 (2C); 26.16 (2C); 22.77 (2C); 20.08 (2C); 14.20 (2C). |

B] Following the procedure of Example 1,E] and employing the compound under A] (1.2 g, 3 mmoles), there was obtained a crude which was taken up in ethyl ether, filtrated and dried under vacuum to provide the title product (m.p.—253°–253.5° C.)

| Elemental analysis: | C | H | N | Cl |
|---|---|---|---|---|
| calculated | 58.33 | 10.64 | 5.92 | 14.97 |
| found | 58.54 | 11.32 | 5.86 | 14.71 |

| | |
|---|---|
| $^1$H-NMR: | m (2H) 4.76; m (8H) 2.98; m (12H) 1.75 ÷ 1.55; m (14H) 1.36 ÷ 1.19; d (6H) 1.25; t (6H) 0.82. |
| $^{13}$C-NMR: | 157.78; 78.53 (2C); 50.45 (2C); 49.92 (2C); 34.74 (2C); 33.32 (2C); 28.26 (2C); 24.59 (2C); 24.35 (2C); 21.75 (2C); 21.66 (2C); 16.11 (2C). |

EXAMPLE 12

5-(N,N-Dibutylamino)-2-pentyl-3'-(N',N'-dibutylamino)-propyl carbonate dihydrochloride A] The compound of Example 10,A] (7 g, 0.032 mole), dissolved in 20 ml of dichloromethane, was added to a solution of CDI (5.8 g, 0.035 mole) dissolved in 50 ml of dichloromethane. The reaction mixture was stirred for 1 hour at room temperature, and sequentially washed with water (3×30 ml), anhydrified over sodium sulfate, and then added to a mixture of 3-(N,N-dibutylamino)propanol (6.8 g, 0.036 mole), prepared as described in EP-B-0 423 151, dissolved in 60 ml of THF, in the presence of sodium (200 mg), previously stirred for 1 hour at room temperature. After filtering off the remaining sodium, the reaction mixture was washed with water (2×50 ml), then with 0.05N HCl (4×30 ml), and lastly with further 50 ml of water. From the organic phase, after anhydrifying over sodium sulfate and evaporation to dryness there were obtained 6.26 g (yield: 45%) of 5-(N,N-dibutylamino)-2-pentyl-3'-(N',N'-dibutylamino)propylcarbonate.

| Elemental analysis: | C | H | N |
|---|---|---|---|
| calculated | 70.04 | 12.23 | 6.63 |
| found | 69.74 | 12.48 | 6.66 |

| | |
|---|---|
| $^1$H-NMR: | m (1H) 4.76; t (2H) 4.16; t (2H) 2.48; m (10H) 2.42 ÷ 2.33; m (22H) 1.86 ÷ 1.19; d (3H) 1.28; m (12H) 0.90. |
| $^{13}$C-NMR: | 155.11; 75.28; 66.53; 54.03 (4C); 53.97; 50.47; 33.97; 29.51 (2C); 29.43 (2C); 26.80; 23.19; 20.90 (2C); 20.83 (2C); 20.12; 14.24 (4C). |

B] Following the procedure of Example 1,E] and using the compound under A] (1.3 g, 3 mmoles), there was obtained a crude which, taken up in ethyl ether, filtered and dried under vacuum provided the title product (m.p.—74°–77° C.)

| Elemental analysis: | C | H | N | Cl |
|---|---|---|---|---|
| calculated | 59.86 | 10.85 | 5.58 | 14.14 |
| found | 57.37 | 10.95 | 5.51 | 13.72 |

| | |
|---|---|
| $^1$H-NMR: | m (1H) 4.77; m (2H) 4.21; m (12H) 3.26 ÷ 3.04; m (2H) 2.08; (12H) 1.78 ÷ 1.52; m (8H) 1.33; d (3H) 1.26; t (12H) 0.89. |
| $^{13}$C-NMR: | 157.90; 78.84; 68.02; 55.72 (2C); 55.61 (2C); 55.14; 52.54; 34.67; 28.08 (4C); 25.64; 22.15 (4C); 22.08; 21.72; 15.96 (4C). |

EXAMPLE 13

Di-[(6-N,N--diethylamino)hexyl] carbonate dihydrochloride hydrate

A] Thionyl chloride (22.5 ml, 0.31 mole) was dropped at 0° C. in absolute ethanol (300 ml). At the end of the addition, 6-bromohexanoic acid (30 g, 0.153 mole) was added in small portions, then the mixture was stirred for 5 hours at room temperature and evaporated to dryness while taking it up in ethanol 2 times. The ethyl 6-bromohexanoate thus obtained was used as such in the next step.

B] A mixture of the compound under A] (34 g, 0.15 mole) and diethylamine (80 ml, 0.77 mole) was refluxed for 2 hours, then the diethylamine in excess was eliminated, and the residue taken up with ethyl ether while filtering off the formed salts. The ether solution was extracted with 1N HCl, the aqueous phase was washed with ethyl ether, alkalinized with concentrated sodium hydroxide and extracted with ethyl ether. The organic phase was anhydrified over sodium sulfate and evaporated thus giving 25.5 g (yield: 78%) of ethyl 6-(N,N-diethylamino)-hexanoate which was used as such in the subsequent step.

C] At 0° C., a solution of the compound under B] (24 g, 0.116 mole) in THF (100 ml) was added to a suspension of lithium aluminium hydride (5.8 g, 0.155 mole) dissolved in 200 ml of THF. The mixture was stirred for 24 hours at room temperature then slowly added dropwise with a mixture of THF (18 ml) and water (2.2 ml), followed by 20% sodium hydroxide (6 ml) and water (23 ml). The formed solid was filtered off and the solvents evaporated off. The crude was purified by distillation under vacuum, thus obtaining 15.4 g (yield: 77%) of 6-(N,N-diethylamino)-hexanol (b.p.—102°–105° C./1.5 mmHg).

| Elemental analysis: | C | H | N |
|---|---|---|---|
| calculated | 69.31 | 13.38 | 8.08 |
| found | 69.09 | 13.59 | 7.99 |

| | |
|---|---|
| $^1$H-NMR: | m (2H) 3.58; q (4H) 2.49; m (2H) 2.38; m (8H) 1.61 ÷ 1.24; t (6H) 0.94. |
| $^{13}$C-NMR: | 62.73; 52.85; 46.85 (2C); 32.83; 27.51; 26.96; 25.75; 11.55 (2C). |

D] A solution of the compound under in C] (17 g, 5 0.098 mole) dissolved in 50 ml of dichloromethane was slowly added with metallic sodium (210 mg) in small pieces. The reaction mixture was stirred for 1 hour at room temperature, then added with a solution of CDI (7.95 g, 0.049 mole) in dichloromethane (80 ml) and stirred for 24 hours. The unreacted solid was filtered off and the organic phase was washed with water (2×80 ml), anhydrified over sodium sulfate and evaporated. The resultant crude was taken up in ethyl ether, then treated with 0.03N HCl (3×100 ml). The organic phase was anhydrified over sodium sulfate and evaporated thus obtaining 14 g (yield: 77%) of di-[(6-N,N-di-ethylamino)hexyl carbonate.

| Elemental analysis: | C | H | N |
|---|---|---|---|
| calculated | 67.70 | 11.90 | 7.52 |
| found | 67.82 | 12.01 | 7.51 |

| | |
|---|---|
| $^1$H-NMR: | t (4H) 4.10; q (8H) 2.49; m (4H) 2.38; m (4H) 1.66; m (12H) 1.51 ÷ 1.20; t (12H) 0.99. |
| $^{13}$C-NMR: | 155.52; 68.07 (2C); 52.97 (2C); 47.00 (4C); 28.81 (2C); 27.45 (2C); 27.01 (2C); 25.86 (2C); 11.77 (4C). |

E] Following the procedure of Example 1,E] and using the compound under D] (1.1 g, 3 mmoles), there was obtained a crude which was taken up in ethyl ether, filtrated and dried under vacuum to provide the title compound (m.p.—81°–85° C.)

| Elemental analysis: | C | H | N | Cl |
|---|---|---|---|---|
| calculated | 54.42 | 10.44 | 6.04 | 15.30 |
| found | 55.48 | 10.26 | 5.96 | 14.98 |

| | |
|---|---|
| $^1$H-NMR: | t (4H) 4.13; q (8H) 3.17; m (4H) 3.08; m (8H) 1.74 ÷ 1.59; m (8H) 1.46 ÷ 1.33; t (12H) 1.24. |
| $^{13}$C-NMR: | 159.03; 71.46 (2C); 54.49 (2C); 50.16 (4C); 30.47 (2C); 28.23 (2C); 27.32 (2C); 26.04 (2C); 11.08 (4C). |

EXAMPLE 14

Di-[(5-N,N-dibutylamino)pentyl] carbonate dihydrochloride hydrate

A] Starting from 5-bromopentanoic acid (50 g, 0.276 mole) and thionyl chloride (39 ml, 0.552 mole) in absolute ethanol (500 ml) and following the procedure of Example 13,A], there were obtained 62.7 g of ethyl 5-bromopentanoate (quantitative yield) which was used as such in the next step.

B] Starting from the compound under A] (60 g, 0.28 mole) and dibutylamine (97 ml, 0.574 mole) and following the procedure of Example 13,B], there were obtained 42.3 g of ethyl 5-(N,N-dibutylamino)pentanoate (yield: 57%) which was used as such in the following step.

C] Starting from the compound under B] (42.3 g, 0.16 mole) and lithium aluminium hydride (9.3 g, 0.246 mole) in THF (120+250 ml), and following the procedure of Example 13,C], there were obtained 36 g of a crude which was purified by distillation under vacuum to give 27.9 g of 5-(N,N-dibutylamino)-pentanol (yield 81%) (b.p.— 104°–105° C./1 mmHg).

| Elemental analysis: | C | H | N |
|---|---|---|---|
| calculated | 72.50 | 13.57 | 6.50 |
| found | 72.36 | 13.70 | 6.45 |

| | |
|---|---|
| $^1$H-NMR: | t (2H); 3.61; m (6H) 2.43 ÷ 2.34; m (14H) 1.64 ÷ 1.18; t (6H) 0.89. |
| $^{13}$C-NMR: | 62.71; 54.23; 54.00 (2C); 32.67; 29.07 (2C); 26.75; 23.86; 20.97 (2C); 14.24 (2C). |

D] Starting from the compound under C] (20 g, 93 mmoles), CDI (7.5 g, 46.5 mmoles) and metallic sodium (214 mg, 9.3 mmoles) in dichloromethane (100+70 ml), and following the procedure of Example 13,D], 12.2 g of di-[(5-N,N- dibutylamino)pentyl] carbonate (yield: 58%) were obtained.

| Elemental analysis: | C | H | N |
|---|---|---|---|
| calculated | 71.00 | 12.36 | 6.13 |
| found | 70.79 | 12.46 | 6.10 |

| | |
|---|---|
| $^1$H-NMR: | t (4H) 4.09; m (12H) 2.40 ÷ 2.31; m (4H) 1.66; m (24H) 1.48 ÷ 1.17; t (12H) 0.88. |
| $^{13}$C-NMR: | 155.48; 68.06 (2C); 54.07 (6C); 29.41 (4C); 28.81 (2C); 26.93 (2C); 23.88 (2C); 20.89 (4C); 14.22 (4C). |

E] Following the procedure of Example 1,E] and using the compound under D] (1.59 g, 3 mmoles), there was obtained a crude which was taken up in ethyl ether, filtrated and dried under vacuum to give the title compound (m.p.—71°–72° C.).

| Elemental analysis: | C | H | N | Cl |
|---|---|---|---|---|
| calculated | 59.21 | 11.04 | 5.11 | 12.95 |
| found | 60.74 | 11.35 | 5.08 | 13.14 |

| | |
|---|---|
| $^1$H-NMR: | t (4H) 4.11; m (12H) 3.07; m (16H) 1.75 ÷ 1.52; m (12H) 1.44 ÷ 1.21; t (12H) 0.86. |
| $^{13}$C-NMR: | 158.87; 71.11 (2C); 55.56 (4C); 55.45 (2C); 30.21 (4C); 28.08 (4C); 25.66 (2C); 25.06 (2C); 22.15 (4C); 15.65 (4C). |

EXAMPLE 15

Di-[3-(piperidin-1'-yl)propyl] carbonate

A] A solution of piperidine (58 ml, 0.58 mole) in methanol (600 ml) was added, at 0° C., with methyl acrilate (263 ml, 2.9 moles). The reaction mixture was stirred for 2 hours at room temperature, then evaporated to dryness to give 98.5 g of methyl 3-(piperidin-1'-yl)propanoate (yield: 99%) which was used as such in the next step.

B] Starting from the compound under A] (98.4 g, 0.57 mole) and lithium aluminium hydride (30.7 g, 0.81 mole) in THF (244+627 ml), and following the procedure of Example 13,C], there were obtained 81 g of a crude which was distilled under vacuum to give 70 g of 3-(piperidin-1'-yl)propanol (yield: 85%) (p.e.—55°–60° C./0.6 mmHg).

| Elemental analysis: | C | H | N |
|---|---|---|---|
| calculated | 67.09 | 11.96 | 9.18 |
| found | 66.85 | 12.04 | 9.73 |

| $^1$H-NMR: | m (2H) 3.77; m (2H) 2.53; m (4H) 2.42; m (2H) 1.67; m (6H) 1.60 ÷ 1.37. |
|---|---|
| $^{13}$C-NMR: | 64.69; 59.54; 54.48 (2C); 26.87; 25.88 (2C); 24.09. |

C] Starting from the compound under B] (20 g, 0.139 mole), CDI (11.3 g, 0.07 mole) and metallic sodium (260 mg, 11.3 mmoles) in dichloromethane (50+117 ml), according to the procedure of Example 13,D], there were obtained 12 g of the title product (yield: 55%).

| Elemental analysis: | C | H | N |
|---|---|---|---|
| calculated | 79.96 | 8.29 | 5.49 |
| found | 79.64 | 8.42 | 5.57 |

| $^1$H-NMR: | t (4H) 4.16; m (4H) 2.37; m (8H) 2.35; m (4H) 1.85; m (12H) 1.62 ÷ 1.35. |
|---|---|
| $^{13}$C-NMR: | 155.12; 66.52; 55.42; 54.43 (2C); 26.14; 25.85 (2C); 24.28. |

EXAMPLE 16

Di-[3-(N-methyl-N-benzylamino)propyl] carbonate dihydrochloride hydrate

A] Using N-methylbenzylamine (53 ml, 0.41 mole) and methyl acrilate (184 ml, 2.05 mole) in 430 ml of methanol, according to the procedure of Example 15,A], there were obtained 85 g (quantitative yield) of methyl 3-(N-methyl-N-benzylamino)propanoate which was used as such in the next step.

B] Using the compound under A] (85 g, 0.41 mole) and lithium aluminium hydride (21 g, 0.55 mole) in THF (234+547 ml), according to Example 13,C], there were yielded a crude which, distilled under vacuum, gave 62.4 g of 3-(N-methyl-N-benzylamino)-propanol (yield: 85%) (b.p.—107°–110° C./1.5 mmHg).

| Elemental analysis: | C | H | N |
|---|---|---|---|
| calculated | 73.70 | 9.56 | 7.81 |
| found | 73.18 | 9.64 | 7.93 |

| $^1$H-NMR: | m (5H) 7.38 ÷ 7.21; m (2H) 3.78; s (2H) 3.52; m (2H) 2.62; m (2H) 1.74. |
|---|---|
| $^{13}$C-NMR: | 137.92; 128.95 (2C); 128.29 (2C); 127.14; 64.56; 62.82; 57.76; 41.84; 27.62. |

C] Starting from the compound under B] (20 g, 0.11 mole), CDI (9 g, 0.055 mole) and metallic sodium (209 mg, 9 mmoles) in dichloromethane (50+94 ml), and following the procedure of Example 13,D], there were obtained 14.9 g of di-[3-(N-methyl-N-benzylamino)-propyl] carbonate (yield: 70%).

| Elemental analysis: | C | H | N |
|---|---|---|---|
| calculated | 71.84 | 8.39 | 7.29 |
| found | 71.60 | 8.41 | 7.17 |

| $^1$H-NMR: | m (10H) 7.33 ÷ 7.23; t (4H) 4.20; s (4H) 3.49; (4H) 2.48; s (6H) 2.19; m (4H) 1.88. |
|---|---|
| $^{13}$C-NMR: | 155.12; 138.96 (2C); 128.77 (4C); 128.08 (4C); 126.80 (2C); 66.19 (2C); 62.26 (2C); 53.43 (2C); 41.92 (2C); 26.55. |

D] Following the procedure of Example 1,E] and using the compound under C] (1.15 g, 3 mmoles), there was obtained the title product as an oil.

| Elemental analysis: | C | H | N | Cl |
|---|---|---|---|---|
| calculated | 57.87 | 8.02 | 5.87 | 14.85 |
| found | 57.81 | 8.09 | 5.61 | 14.17 |

| $^1$H-NMR: | m (19H) 7.46; s (4H) 4.31; t (4H) 4.17; m (4H) 3.22; s (6H) 2.79; m (4H) 2.13. |
|---|---|
| $^{13}$C-NMR: | 157.92; 133.81 (4C); 133.10 (2C); 132.24 (4C); 131.84 (2C); 68.16 (2C); 62.17 (2C); 55.21 (2C); 42.29 (2C); 26.03 (2C). |

EXAMPLE 17

Di-[3-(N,N-dibenzylamino)propyl] carbonate dihydrochloride

A] Starting from dibenzylamine (48.7 ml, 0.25 mole) and methyl acrilate (112.5 ml, 1.25 moles) in 259 ml of methanol, and following the procedure of Example 15,A], there were obtained 70 g (yield: 99%) of methyl 3-(N,N-dibenzylamino)-propanoate which was used as such in the next step.

B] Starting from the compound under A] (70 g, 0.247 mole) and lithium aluminium hydride (12.6 g, 0.33 mole) in THF (210+490 ml), and following the procedure of Example 13,C], there were obtained 63.7 g of a crude which was distilled under vacuum to give 50 g of 3-(N,N-dibenzylamino)propanol (yield: 79%) (b.p.—150°–152° C./1 mmHg).

| Elemental analysis: | C | H | N |
|---|---|---|---|
| calculated | 79.96 | 8.29 | 5.49 |
| found | 79.74 | 8.35 | 5.57 |

| $^1$H-NMR: | m (10H) 7.36 ÷ 7.26; m (2H) 3.66; s (4H) 3.59, m (2H) 2.65; m (2H) 1.77. |
|---|---|
| $^{13}$C-NMR: | 138.16 (2C); 129.02 (4C); 128.34 (4C); 127.13 (2C); 63.76; 58.49 (2C); 53.05; 27.88. |

C] Starting from the compound under B] (20 g, 0.078 mole), CDI (6.35 g, 0.039 mole) and metallic sodium (147 mg, 6.4 mmoles) in dichloromethane (50+60 ml), and following the procedure of Example 13,D], there were obtained 14.8 g of di-(3-(N,N-dibenzylamino)propyl] carbonate (yield: 71%).

| Elemental analysis: | C | H | N |
|---|---|---|---|
| calculated | 78.33 | 7.51 | 5.22 |
| found | 78.18 | 7.57 | 5.08 |

¹H-NMR: m (20H) 7.38 ÷ 7.19; m (4H) 4.11; s (8H) 3.56; m (4H) 2.51; m (4H) 1.84.
¹³C-NMR: 154.90; 139.37 (4C); 128.61 (8C); 128.08 (8C); 126.74 (4C); 66.04 (2C); 58.24 (4C); 49.48 (2C); 26.22 (2C).

D] Following the procedure of Example 1,E] and using the compound under C] (1.6 g, 3 mmoles), there was obtained a crude which was taken up in ethyl ether, filtrated and dried under vacuum to provide the title compound (m.p.—190°–192° C.).

| Elemental analysis: | C | H | N | Cl |
|---|---|---|---|---|
| calculated | 68.96 | 6.94 | 4.60 | 11.63 |
| found | 68.86 | 7.03 | 4.60 | 11.20 |

¹H-NMR: m (20H) 7.46 ÷ 7.38; m (8H) 4.33; t (4H) 4.02; m (4H) 3.12; m (4H) 2.07.
¹³C-NMR: 157.64; 133.95 (8C); 133.11 (4C); 132.28 (8C); 131.72 (4C); 68.09 (2C); 60.20 (4C); 51.50 (2C); 25.52 (2C).

EXAMPLE 18

Di-[4-(N,N-diisopropylamino)butyl] carbonate dihydrochloride

A] A solution of succinic anhydride (30 g, 0.299 mole) in dichloromethane (300 ml) was slowly added with diisopropylamine (46 g, 0.328 mole) in dichloromethane (200 ml). The mixture was refluxed for 5 hours, then the organic phase was washed with 1N HCl (2×200 ml) and water (300 ml), anhydrified over sodium sulfate and evaporated. The crude was taken up in ethyl ether, the formed solid was filtered off and the solvent evaporated to give 40.7 g of mono-(N,N-diisopropyl)succinamide (yield: 70%) which was used as such in the next step.

B] Starting from the compound under A] (36 g, 0.178 mole) and lithium aluminium hydride (27 g, 0.715 mole) in THF (108+700 ml), and following the procedure of Example 13,C], there were obtained 31.8 g of a crude which was distilled under vacuum to give 22 g of 4-(N,N-diisopropylamino)butanol (yield: 71%) (b.p.—80°–83° C./1.5 mmHg).

| Elemental analysis: | C | H | N |
|---|---|---|---|
| calculated | 69.31 | 13.38 | 8.08 |
| found | 69.25 | 13.50 | 7.79 |

¹H-NMR: m (2H) 3.54; m (2H) 3.11; m (2H) 2.48; m (4H) 1.65; d (12H) 1.05.
¹³C-NMR: 62.87; 47.66 (2C); 45.04; 32.60; 27.73; 20.14 (4C).

C] Starting from the compound under B] (17 g, 0.098 mole), CDI (7.95 g, 0.049 mole) and metallic sodium (210 mg, 9.1 mmoles) in dichloromethane (50+80 ml), and following the procedure of Example 13,D], there were obtained 10.4 g of di-[4-(N,N-diisopropylamino)butyl] carbonate (yield: 57%).

| Elemental analysis: | C | H | N |
|---|---|---|---|
| calculated | 67.70 | 11.90 | 7.52 |
| found | 68.02 | 12.08 | 7.60 |

¹H-NMR: t (4H) 4.12; m (4H) 2.98; m (4H) 2.39; m (8H) 1.73 ÷ 1.36; d (24H) 0.97.
¹³C-NMR: 155.55; 68.23 (2C); 48.24 (4C); 44.61 (2C); 27.22 (2C); 26.67 (2C); 20.84 (8C).

D] Following the procedure of Example 1,E] and using the compound under C] (1.12 g, 3 mmoles), there was obtained a crude which was taken up in ethyl ether, filtered and dried under vacuum to give the title compound (m.p.—124°–129° C.).

| Elemental analysis: | C | H | N | Cl |
|---|---|---|---|---|
| calculated | 56.62 | 10.41 | 6.29 | 15.92 |
| found | 56.11 | 10.58 | 6.11 | 15.71 |

¹H-NMR: m (1H) 4.17; m (4H) 3.68; m (4H) 3.11; m (8H) 1.75; d (24H) 1.30.
¹³C-NMR: 158.63; 70.55 (2C); 57.88 (4C); 49.80 (2C); 28.12 (2C); 26.68 (2C); 20.70 (4C); 19.08 (4C).

EXAMPLE 19

Di-3-(N,N-dibutylamino)propyl carbonate dihydrochloride

A] A solution of dibutylamine (1 l, 5.88 moles) in methanol (2.35 l), kept under stirring at 50° C., was slowly added dropwise with methyl acrilate (1.051 l, 11.76 moles). The mixture was then brought to room temperature and kept under stirring for 1 hour, thereafter 1.174 l of dichloromethane were added and the product extracted with 4.7 l of 3N HCl. The organic phase was washed with water (3×2.35 l). The aqueous phase was brought to pH-9 with 5N sodium hydrate and extracted with dichloromethane (2×2.35 l). The organic phase was washed with 2.35 l of distilled water, then anhydrified over sodium sulfate and evaporated under vacuum thus obtaining 1197 g of methyl N,N-dibutyl-3-amino-propionate (yield: 94.5%) as a pale yellow oil which was used as such in the next step.

B] RED-Al@ (3.4M solution of 70% sodium-bis(2-methoxyethoxy)aluminium hydride in toluene Aldrich) (2.5 l) was dissolved in dry toluene (3.26 l) at room temperature under inert atmosphere, and slowly added with the compound under A] (1000 g, 4.64 moles) dissolved in dry toluene (5.13 l), while controlling the temperature under 40° C. The reaction mixture was stirred for 1 hour at room temperature, and the excess of reducing agent was decomposed by adding 4 l of 2N sodium hydrate, while maintaining the temperature under 3° C. The phases were separated and the organic one was washed with 2.6 l of water, anhydrified over sodium sulfate and evaporated under vacuum to give 756 g of a colourless oil which was distilled under vacuum and provided 708 g (yield: 82%) of 4-(N-dibutylamino) propanol (b.p.—65°–68° C./0.3 mmHg) as an oil.

C] A solution of the compound under B] (1000 g, 5.33 moles) in THF (2.4 l) under inert atmosphere, was added with metallic sodium (10 g) at room temperature, then reacted for 30 minutes. CDI (440 g, 2.66 moles) in dichloromethane (4.6 l) was slowly added, while maintaining the room temperature, the mixture was stirred for 1 day, filtered and added with 5 l of water. The organic phase was washed with 0.03N HCl (4×3 l), then with water (2×5 l), anhydrified over sodium sulfate and evaporated under vacuum to give 920 g of di-3-(N,N-dibutylamino)propyl carbonate (yield: 86.2%).

| Elemental analysis: | C | H | N |
|---|---|---|---|
| calculated | 68.95 | 12.08 | 6.99 |
| found | 69.22 | 12.15 | 7.082 |

| | |
|---|---|
| $^1$H-NMR: | t (4H) 4.16; t (4H) 2.46; t (4H) 2.36; q (4H) 1.77; m (16H) 1.45 ÷ 1.17; t (12H) 0.88. |
| $^{13}$C-NMR: | 155.57; 66.52; 53.81; 29.20; 26.48; 20.51; 13.90. |

D] Following the procedure of Example 1,E] and using the compound under C] (1.2 g, 3 mmoles) there was obtained a crude which was taken up in ethyl ether, filtered and dried under vacuum to provide the title compound (m.p.—77°–80° C.).

| Elemental analysis: | C | H | N | Cl |
|---|---|---|---|---|
| calculated | 58.33 | 10.64 | 5.92 | 14.97 |
| found | 57.30 | 11.11 | 5.75 | 14.68 |

| | |
|---|---|
| $^1$H-NMR: | m (4H) 4.24; m (4H) 3.26; m (8H) 3.15; m (4H) 2.10; m (8H) 1.66; m (8H) 1.35; t (12H) 0.94. |
| $^{13}$C-NMR: | 158.10; 68.28 (2C); 55.70 (4C); 52.60 (2C); 28.07 (4C); 25.66 (2C); 22.15 (4C); 15.72 (4C). |

EXAMPLE 20

Bis-(N,N-dibutylamino)butyl carbonate dihydrochloride

A] A solution of succinic anhydride (588 g, 5.88 moles) in dichloromethane (4.8 l) was stirred for 30 minutes at room temperature, then slowly added with a solution of dibutylamine (1 l, 5.88 moles) in dichloromethane (1.6 l), while maintaining the temperature under 40° C. The reaction mixture was stirred for 4 hours at room temperature, then washed with 1 l of 1N HCl. The phases were separated and the organic one was washed with water (4×1 l), anhydrified over sodium sulfate and evaporated under vacuum to give 1320 g (yield: 99%) of mono-N,N-dibutylsuccinimide as a pale yellow thick oil.

B] A mixture of RED-Al@ (4.9 1 l) in anhydrous toluene (4 l) was slowly added with a solution of the compound under A] (1000 g, 4.36 moles) in anhydrous toluene (8 l), while maintaining the temperature under 40° C. The reaction mixture was stirred for 1 hour at room temperature, then the reducing agent in excess was decomposed by adding 4 l of 2N sodium hydrate, while cooling the reactor to 3° C. The phases were separated and the organic one was washed with 2 l of water, then anhydrified over sodium sulfate and evaporated under vacuum to give 800 g of a crude which by distillation under vacuum provided 750 g (yield: 85%) of 4-(N-dibutylamino)butanol (b.p.—75°–80° C./0.3 mmHg).

C] A mixture of the compound under B] (1000 g, 5 moles) in THF (2.35 l), under inert atmosphere, was added with metallic sodium (11.42 g, 0.5 mole) and reacted for 24 hours at room temperature. Then a solution of CDI (452 g, 2.7 moles) in dichloromethane (4.6 l) was slowly added therein, while maintaining the temperature under 30° C. The reaction mixture was left under stirring for 1 hour, the unreacted sodium was filtered off and the filtrate added with 5 l of dichloromethane, then washed with water (2×5 l). The organic phase was washed with 1N HCl (3×1.8 l), then with water (2×5 l), anhydrified over sodium sulfate and evaporated under vacuum to provide 854 mg of bis-(N,N-dibutylamino)butyl carbonate as an oil.

| Elemental analysis: | C | H | N |
|---|---|---|---|
| calculated | 68.95 | 12.08 | 6.99 |
| found | 69.05 | 11.93 | 6.76 |

| | |
|---|---|
| $^1$H-NMR: | t (4H) 4.10; m (4H) 2.37; m (8H) 2.35; m (24H) 1.71 ÷ 1.15; t (12H) 0.86. |
| $^{13}$C-NMR: | 155.63; 67.93 (2C); 53.79 (2C); 29.18 (4C); 26.62 (2C); 23.27 (2C); 20.56 (2C); 13.89 (4C). |

D] Following the procedure of Example 1,E] and using the compound under C] (1.5 g, 3 mmoles) there was obtained a crude which was taken up in ethyl ether, filtered and dried under vacuum to provide the compound in title (m.p.—98°–101° C.)

| Elemental analysis: | C | H | N | Cl |
|---|---|---|---|---|
| calculated | 59.86 | 10.85 | 5.58 | 14.14 |
| found | 59.47 | 10.97 | 5.59 | 13.93 |

| | |
|---|---|
| $^1$H-NMR: | m (4H) 4.19; m (12H) 3.20 ÷ 3.08; m (16H) 1.85 ÷ 1.58; m (8H) 1.35; t (12H) 0.91. |
| $^{13}$C-NMR: | 158.64; 70.61 (2C); 55.63 (4C); 55.08 (2C); 28.11 (4C); 27.97 (2C); 22.77 (2C); 22.19 (4C); 15.73 (4C). |

EXAMPLE 21

Di-5-(N-benzyl-N-methylamino)-2-pentyl carbonate dihydrocloride

A] Starting from 10 g (0.086 mole) of levulinic acid, 11.8 ml (0.086 mole) of triethylamine, 11.2 ml (0.086 mole) of isobutyl chloroformate and 13.3 ml (0.103 mole) of N-methyl-benzylamine in 200 ml of acetone, and following the procedure of Example 6,B], there were obtained 16.7 g (yield: 88%) of N-benzyl-N-methyl-4-oxo-pentanamide.

B] From 16.7 g (0.076 mole) of the compound under A] and 4.3 g (0.114 mole) of lithium aluminium hydride in 150 ml of THF, following the procedure of Example 6,C], there were obtained 11 g (yield:69%) of crude 5-(N-benzyl-N-methylamino)-2-pentanol which was used as such in the next step.

C] A solution of 3.4 g (0.016 mole) of the compound under B] in 50 ml of chloroform was added with 2.9 g (0.018 mole) of CDI at room temperature. The reaction mixture was stirred for 3 hours, then washed with 100 ml of water, and the solvent removed under vacuum to give 3.5 g (0.012 mole) of activated product which was dissolved in 20 ml of THF and added to a solution of 2.4 g (0.012 mole) of the compound under B] in 15 ml of THF, treated at 0° C. with a 1.6M solution of butyl-lithium (7.3 ml 0.012 mole). The resultant mixture was stirred overnight at room temperature, then the solvent was removed under vacuum and the crude thus obtained was taken up in 100 ml of chloroform and washed with 100 ml of water, then more times with 0.03N HCl. The organic phase was anhydrified over sodium sulfate and evaporated, and the resultant crude was purified by chromatography on a silica gel column (230–400 mesh; eluent: hexane/ethyl acetate 3:7) to give 1.3 g (yield: 25%) of the title product.

| Elemental analysis: | C | H | N |
|---|---|---|---|
| calculated | 73.60 | 9.15 | 6.36 |
| found | 73.51 | 8.99 | 6.87 |

$^1$H-NMR: m (10H) 7.43 ÷ 7.16; m (2H) 4.77; m (4H) 3.47; m (4H) 2.38; s (6H) 2.17; m (8H) 1.71 ÷ 1.50; d (6H) 1.28.
$^{13}$C-NMR: 154.74; 139.32 (2C); 129.14 (2C); 128.35 (2C); 127.05 (2C); 75.00 (2C); 62.51 (2C); 57.22 (2C); 42.27 (2C); 33.82 (2C); 23.37 (2C); 20.15 (2C).

D] Following the procedure of Example 1,E] and using the compound under C] there was obtained a crude which, taken up in ethyl ether, filtered and dried under vacuum, provided the compound in title.

| Elemental analysis: | C | H | N | Cl |
|---|---|---|---|---|
| calculated | 61.01 | 8.43 | 5.27 | 13.34 |
| found | 60.92 | 8.46 | 5.30 | 13.22 |

$^1$H-NMR: m (10H) 7.50 ÷ 7.40; m (2H) 4.71; m (4H) 4.37 ÷ 4.15; m (4H) 3.23 ÷ 2.96; s (3H) 2.76; s (3H) 2.74; m (8H) 1.87 ÷ 1.52; d (6H) 1.22.
$^{13}$C-NMR: 157.64; 133.40 (4C); 133.09 (2C); 132.24 (4C); 131.90 (2C); 78.41 (2C); 62.63; 62.51; 57.79 (2C); 42.35 (2C); 34.59 (2C); 22.51 (2C); 21.75; 21.64.

EXAMPLE 22

5-(N,N-dibutylamino)-2-pentyl, 5'-(N-benzyl-N-methylamino)-2-pentyl carbonate dihydrochloride A] The product of Example 10,A] (4.2 g, 0.019 mole) was dissolved in 50 ml of chloroform containing 3.5 g (0.021 mole) of CDI. Such mixture was stirred for 3 hours at room temperature, then washed with water, and the solvent was removed under vacuum yielding 6 g (0.019 mole) of activated product which was dissolved in 20 ml of THF, and added to a solution of 4 g (0.019 mole) of the product of Example 21,B] in 20 ml of THF, and treated at 0° C. with a 1.6M solution of butyl lithium (12 ml, 0.019 mole). The mixture was stirred overnight at room temperature, then the solvent was evaporated under vacuum and the resultant crude taken up in 100 ml of chloroform, washed with 100 ml of water, then more times with 0.03N HCl. The organic phase was anhydrified over sodium sulfate and evaporated, and the resultant crude was purified by chromatography on a silica gel column (230–400 mesh; eluent: chloroform/methanol 9:1) to give 1.8 g (yield: 21%) of the title product.

| Elemental analysis: | C | H | N |
|---|---|---|---|
| calculated | 72.28 | 10.78 | 6.24 |
| found | 72.89 | 10.89 | 6.29 |

$^1$H-NMR: m (5H) 7.42 ÷ 7.17; m (2H) 4.76; m (2H) 3.47; m (8H) 2.43 ÷ 2.34; s (3H) 2.17; m (16H) 1.70 ÷ 1.23; d (6H) 1.28; t (6H) 0.91.
$^{13}$C-NMR: 154.72; 139.34; 129.12 (2C); 128.33 (2C); 127.02; 75.07; 75.00; 62.52; 57.22; 53.97 (2C); 53.92; 42.25; 34.00; 33.81; 29.34 (2C); 23.37; 23.11; 20.89 (2C); 20.14 (2C); 14.26 (2C).

B] Following the procedure of Example 1,E] and using the compound under C] there was obtained a crude which was taken up in ethyl ether, filtered and dried under vacuum to give the compound in title.

| Elemental analysis: | C | H | N | Cl |
|---|---|---|---|---|
| calculated | 62.17 | 9.66 | 5.37 | 13.59 |
| found | 60.61 | 9.61 | 5.04 | 12.69 |

$^1$H-NMR: m(5H)7.46; m(2H)4.74; m(2H)4.30; m(8H) 3.18÷3.02; s(3H)2.77; m(12H)1.78÷1.52; m (10H)1.39÷1.21; t(3H)0.87; t(3H)0.86.
$^{13}$C-NMR: 157.60; 133.82(2C); 133.10; 132.24(2C); 131.91; 78.43(2C); 62.53; 57.76; 55.61; 55.54; 55.09; 42.36; 34.67; 34.60; 28.08 (2C); 22.52; 22.15(2C); 22.06; 21.80; 21.68; 15.69(2C).

EXAMPLE 23

Bis-3-(N,N-di hexylamino)propyl carbonate

The title product was prepared substantially following the procedure of Example 19,A–C].

| Elemental analysis: | C | H | N |
|---|---|---|---|
| calculated | 74.36 | 10.47 | 5.59 |
| found | 73.90 | 13.01 | 5.60 |

$^1$H-NMR: t(4H)4.14; t(4H)2.44; m(8H)2.32; m(4H) 1.75; m(32H)1.41÷1.18; t(12H) 0.85.
$^{13}$C-NMR: 155.59; 66.56(2C); 54.14(4C); 50.26(2C); 31.75(4C); 27.11(4C); 26.99(4C); 26.45 (2C); 22.55(4C); 13.92(4C).

EXAMPLE 24

Bis-3-(N,N-diethylamino)propyl carbonate

Starting from diethylamine and methyl acrilate and substantially following the procedure of Example 19,A–C], the title compound was obtained.

$^1$H-NMR: t (4H) 4.13; m (12H) 2.46; m (4H) 1.75; t (12H) 0.95.

$^{13}$C-NMR: 156.53; 66.51 (2C); 49.04 (2C); 46.82 (4C); 26.40 (2C); 11.58 (4C).

EXAMPLE 25

Bis-2-(N,N-dihexylamino)ethyl carbonate

The title product was prepared starting from ethanolamine and butyl bromide, and substantially following the procedure of Example 19,A–C].

| Elemental analysis: | C | H | N |
|---|---|---|---|
| calculated | 73.06 | 10.99 | 5.87 |
| found | 70.79 | 11.95 | 6.05 |

| | |
|---|---|
| ¹H-NMR: | t(4H)4.13; m(4H)2.68; m(8H)2.42; m (32H)1.46÷1.17; t(12H)0.85. |
| ¹³C-NMR: | 155.55; 66.04(2C); 54.77(4C); 52.15(2C); 31.70(4C); 27.08(4C); 26.98(4C); 22.51 (4C); 13.88(4C). |

EXAMPLE 26

Di-5-(N-piperidyl)pent-2-yl carbonate dihydrochloride

A] Using levulinic acid (17.6 ml, 170 mmoles) and piperidine (17 ml, 170 mmoles), and following the procedure of Examples 10,A–B] di-5-(N-piperidyl)pent-2-yl carbonate was obtained.

| Elemental analysis: | C | H | N |
|---|---|---|---|
| calculated | 68.44 | 10.94 | 7.60 |
| found | 68.90 | 11.20 | 7.80 |

| | |
|---|---|
| ¹H-NMR: | m(2H)4.75; m(8H)2.35; m(20H)1.69÷1.37; d(6H)1.27. |
| ¹³C-NMR: | 154.67; 74.94(2C); 59.27(2C); 54.74(4C); 34.10(2C); 26.14(4C); 24.62(2C); 22.93 (2C); 20.08(2C). |

B] Using the compound under A] according to Example 1,E], 9.2 g of the title product were obtained.

| Elemental analysis: | C | H | N | Cl |
|---|---|---|---|---|
| calculated | 57.13 | 9.59 | 6.35 | 16.06 |
| found | 55.34 | 9.68 | 6.18 | 15.72 |

| | |
|---|---|
| ¹H-NMR: | m(2H)4.76; m(4H)3.84; m(4H)3.06; m(4H)2.88; m(20H)1.96÷1.37; d(6H)1.25. |
| ¹³C-NMR: | 157.74; 78.52(2C); 59.33(2C); 56.05(4C); 34.77(2C); 25.71(4C); 24.04(2C); 22.36 (2C); 21.75; 21.65. |

EXAMPLE 27

Di-5-(N,N-diethylamino)pent-2-yl carbonate dihydrochloride dihydrate

A] Starting from levulinic acid (8.8 ml, 86 mmoles) and diethylamine (11 ml, 103 mmoles) and substantially applying the procedure of Example 10,A–B], di-5-(N,N-diethylamino)pent-2-yl carbonate was obtained.

| Elemental analysis: | C | H | N |
|---|---|---|---|
| calculated | 66.24 | 11.70 | 8.13 |
| found | 66.49 | 11.40 | 8.20 |

| | |
|---|---|
| ¹H-NMR: | m(2H)4.75; q(8H)2.49; m(4H)2.39; m(8H)1.66÷1.41; d(3H)1.27; d(3H)1.26; t(12H)0.99. |
| ¹³C-NMR: | 154.69; 74.96(2C); 52.72(2C); 46.98(4C); 34.05(2C); 23.10(2C); 20.11(2C); 11.83 (4C). |

B] Starting from the compound under A] and following the procedure of Example 1,E], 1.7 g of the title product was obtained.

| Elemental analysis: | C | H | N | Cl |
|---|---|---|---|---|
| calculated | 50.32 | 10.22 | 6.18 | 15.64 |
| found | 50.18 | 10.32 | 5.96 | 14.88 |

| | |
|---|---|
| ¹H-NMR: | m(2H)4.78; q(8H)3.17; m(4H)3.11; m(8H)1.81÷1.60; d(6H)1.26; t(12H)1.24. |
| ¹³C-NMR: | 157.77; 78.56(2C); 54.12(2C); 50.23(4C); 34.73(2C); 22.28; 21.79; 21.66(2C); 11.42 (4C). |

EXAMPLE 28

Di-5-(N,N-dihexylamino)pent-2-yl carbonate dihydrochloride

A] Using levulinic acid (17.6 ml, 170 mmoles) and dihexylamine (48 ml, 206 mmoles) and applying the procedure of Example 10,A–B], di-5-(N,N-dihexylamino)pent-2-yl carbonate was obtained.

| Elemental analysis: | C | H | N |
|---|---|---|---|
| calculated | 73.89 | 12.75 | 4.92 |
| found | 74.25 | 13.00 | 5.02 |

| | |
|---|---|
| ¹H-NMR: | m(2H)4.74; m(12H)2.40÷2.31; m(46H)1.70÷1.19; m(12H)0.86. |
| ¹³C-NMR: | 154.70; 74.98(2C); 54.32(4C); 53.96(2C); 34.01(2C); 32.00(4C); 27.44(4C); 27.18 (4C); 23.16(2C); 22.18(4C); 20.11(2C); 14.20(4C). |

B] Using the compound under A] and substantially proceeding according to procedure of Example 1,E], 6.9 g of the title product were obtained.

| Elemental analysis: | C | H | N | Cl |
|---|---|---|---|---|
| calculated | 65.39 | 11.76 | 4.36 | 11.03 |
| found | 62.63 | 11.51 | 4.30 | 10.82 |

EXAMPLE 29

Di-5-(N,N-diisobutylamino)pent-2-yl carbonate

Starting from levulinic acid (13.2 ml, 130 mmoles) and diisobutylamine (26.6 ml, 155 mmoles), and substantially proceeding according to the procedure of Example 10,A–B], 5.3 g of the title product were obtained.

| Elemental analysis: | C | H | N |
|---|---|---|---|
| calculated | 71.00 | 12.36 | 6.13 |
| found | 73.79 | 12.87 | 5.56 |

| | |
|---|---|
| $^1$H-NMR: | m(2H)4.76; t(4H)2.29; d(8H)2.02; m(12H)1.75÷1.33; d(6H)1.27; d(24H)0.85. |
| $^{13}$C-NMR: | 154.78; 75.05(2C); 64.12(4C); 54.97(2C); 33.03(2C); 26.75(4C); 23.24(2C); 21.08 (8C); 20.16(2C). |

EXAMPLE 30

Di-5-(N,N-disec-butylamino)pent-2-yl carbonate

Starting from levulinic acid (13.2 ml, 130 mmoles) and disecbutylamine (26.6 ml, 155 mmoles), and substantially proceeding according to the procedure of Example 10,A–B], 6.7 g of the title product were obtained.

| Elemental analysis: | C | H | N |
|---|---|---|---|
| calculated | 71.00 | 12.36 | 6.13 |
| found | 72.04 | 12.77 | 6.21 |

| | |
|---|---|
| $^1$H-NMR: | m(2H)4.74; m(4H)2.58; m(4H)2.41; m(16H) 1.77÷0.97; d(6H) 1.26; d (6H) 0.94; d (6H)0.91; t(6H)0.85; t(6H)0.84. |
| $^{13}$C-NMR: | 154.78; 75.32+75.27+75.14+74.97(2C); 54.96 (2C); 54.03(2C); 44.61+44.44+44.34+ 44.18(2C); 33.94+33.80+33.67(2C); 29.30 (2C); 28.02(2C); 26.18+26.11+25.94+ 25.89+25.70+25.59(2C); 20.17(2C); 18.16 +18.11(2C); 17.05(2C); 12.16+12.10(4C). |

EXAMPLE 31

Di-6-(N,N-dibutylamino)hex-2-yl carbonate dihydrochloride dihydrate

A] Starting from 4-acetyl-butanoic acid (18.5 ml, 155 mmoles) and dibutylamine (26.6 ml, 155 mmoles), and substantially proceeding according to the procedure of Example 10,A–B] di-6-(N,N-dibutylamino)hex-2-yl carbonate was obtained.

| Elemental analysis: | C | H | N |
|---|---|---|---|
| calculated | 71.85 | 12.47 | 5.78 |
| found | 71.42 | 12.65 | 5.65 |

| | |
|---|---|
| $^1$H-NMR: | m(2H)4.74; m(12H)2.38; m(28H)1.76÷1.19; d(6.H)1.27; t(12H)0.91. |
| $^{13}$C-NMR: | 154.71; 75.10(2C); 54.06(6C); 36.08(2C); 29.38(4C); 27.06(2C); 23.58(2C); 20.93 (4C); 20.05(2C); 14.26(4C). |

B] Starting from the compound under A] and following the procedure of Example 1,E], 5.2 g of the title product were obtained.

| Elemental analysis: | C | H | N | Cl |
|---|---|---|---|---|
| calculated | 58.66 | 11.20 | 4.72 | 11.94 |
| found | 58.22 | 11.95 | 4.69 | 12.37 |

| | |
|---|---|
| $^1$H-NMR: | m(2H)4.75; m(12H)3.09; m(16H)1.54÷1.72; m(12H)1.44÷1.23; d(6H)1.23; t(12H)0.88. |
| $^{13}$C-NMR: | 158.06; 79.10; 79.01; 55.61(4C); 55.41(2C); 37.25(2C); 28.11(4C); 25.80(2C); 24.57 (2C); 22.16(4C); 21.92; 21.18; 15.66(4C). |

EXAMPLE 32

Di-4-(N-tert.butyl-N-methylamino)butyl carbonate dihydrochloride

A] Starting from succinic anhydride (7.5 g, 75 mmoles) and tert-butyl-methylamine (10 ml, 83 mmoles), and substantially applying the procedure of Example 18,A–C], di-4-(N-tert.butyl-N-methylamino)butyl carbonate was obtained.

| Elemental analysis: | C | H | N |
|---|---|---|---|
| calculated | 66.26 | 11.70 | 8.13 |
| found | 66.10 | 12.08 | 7.80 |

| | |
|---|---|
| $^1$H-NMR: | m(4H)4.13; m(4H)2.34; s(6H)2.17; m(8H) 1.75÷1.30; s(18H)1.03. |
| $^{13}$C-NMR: | 155.54; 68.14(2C); 54.16(2C); 50.59(2C); 35.18(2C); 26.91(4C); 26.18(6C); 25.71 (2C). |

B] Starting from the compound under A] and following th procedure of Example 1,E], 800 mg of the title product were obtained.

| Elemental analysis: | C | H | N | Cl |
|---|---|---|---|---|
| calculated | 54.67 | 10.14 | 6.71 | 16.99 |
| found | 53.89 | 10.09 | 6.48 | 16.09 |

| | |
|---|---|
| $^1$H-NMR: | m(4H)4.18; m(8H)3.12; s(6H)2.74; m(8H) 1.96÷1.61; s(18H)1.35. |
| $^{13}$C-NMR: | 158.67; 70.59(2C); 66.74(2C); 53.50(2C); 37.20(2C); 28.09(2C); 26.46(6C); 24.69 (2C). |

EXAMPLE 33

Di-4-(2,6-dimethylpiperidyl)butyl carbonate dihydrochloride

A] Starting from succinic anhydride (13 g, 131 mmoles) and cis-2,6-dimethylpiperidine (20 ml, 144 mmoles) and substantially applying the procedure of Example 18,A–C], di-4-(2,6-dimethylpiperidyl)-butyl carbonate was obtained.

| Elemental analysis: | C | H | N |
|---|---|---|---|
| calculated | 69.65 | 11.18 | 7.06 |
| found | 70.42 | 11.20 | 7.18 |

| | |
|---|---|
| $^1$H-NMR: | m(4H)4.12; m(4H)2.75; m(4H)2.42;m(20H)1.65÷1.20; d(12H)1.09. |

| Elemental analysis: | C | H | N |
|---|---|---|---|
| $^{13}$C-NMR: | 155.42; 68.00(2C); 55.34(4C); 47.71(2C); 35.31(4C); 26.91(4C); 24.91(2C); 21.39 (2C); 20.91(2C). | | |

B] Starting from the compound under A] and following the procedure of Example 1,E], 3.4 g of the title product were obtained.

| Elemental analysis: | C | H | N | Cl |
|---|---|---|---|---|
| calculated | 58.84 | 9.87 | 5.97 | 15.10 |
| found | 57.96 | 10.04 | 5.80 | 15.32 |
| $^1$H-NMR: | m(4H)4.18; m(8H)3.43÷2.96; m(20H) 1.98÷1.47; d(9.6H)1.38; d(2.4H)1.31. | | | |
| $^{13}$C-NMR: | 158.63; 70.64(2C); 61.94(4C); 50.33(2C); 34.94(4C); 27.86(4C); 24.77(2C); 20.49 (2C); 19.60(2C). | | | |

EXAMPLE 34

Di-3-(N,N-diisopropylamino)propyl carbonate dihydrochloride

A] Methyl acrilate (89 ml, 0.988 mmole) was slowly dropped into a solution of diisopropylamine (27.7 ml, 0.198 mmole) in methanol (300 ml) at −10° C. The reaction mixture was brought to room temperature and stirred for 24 hours, then the solvent and the methyl acrilate in excess were evaporated off thus obtaining 37 g of crude methyl 3-(N,N-diisopropylamino)propionate (quantitative yield) which was directly employed in the next step.

B] A solution of the compound under A] (37 g, 0.198 mmole) in THF (150 ml) was dropped into a suspension of litium aluminium hydride (11.2 g, 0.296 mole) in THF (400 ml), at a temperature ranging between 0° C. and 10° C. At the end of the addition, the reaction mixture was stirred at room temperature for 2 hours, the a mixture of THF (34 ml) and water (5 ml) was added followed by a 20% solution of sodium hydroxide (11 ml) and water (44 ml). The formed salts were filtered off and the filtrate was evaporated to dryness. The resulting crude was taken up in dichloromethane, dried over sodium sulfate and evaporated. The crude product was purified by distillation under vacuum (19 mmHg) thus providing 22.7 g of pure 3-(N,N-diisopropylamino)propanol (b.p.: 109°–112° C.) (yield: 72%).

C] A solution of the compound under B] (5 g, 31.4 mmoles) in dichloromethane (15 ml) was added with metallic sodium (72 mg, 3.1 mmoles), then a solution of CDI (2.5 g, 15.7 mmoles) in dichloromethane (30 ml) was dropped therein at room temperature. Such mixture was stirred overnight at the same temperature. The remaining solid was filtered off and the organic phase was washed with water (2×40 ml), then with 0.03M HCl (3×25 ml), then anhydrified over sodium sulfate. The resulting crude was purified by silica gel column chromatography (eluent: chloroform/acetone 7:3) thus obtaining 2.3 g of di-3-(N, N-diisopropylamino)propyl carbonate.

| Elemental analysis: | C | H | N |
|---|---|---|---|
| calculated | 66.24 | 11.70 | 8.13 |
| found | 65.52 | 11.73 | 8.01 |
| $^1$H-NMR: | m(4H)4.17; m(4H)2.98; m(4H)2.51; m(4H) 1.74; d(24H)0.74. | | |
| $^{13}$C-NMR: | 155.60; 66.44(2C); 48.19(4C); 41.08(2C); 29.77(2C); 26.84(8C). | | |

D] The compound under C] was dissolved in chloroform (40 ml) and added with an ether solution of 2N HCl (6.7 ml, 13.4 mmoles). The solution was evaporated to dryness and the resulting solid was taken up three times in ethyl ether, the evaporated again to dryness yielding 3.2 g of the title product as a waxy solid.

| Elemental analysis: | C | H | N | Cl |
|---|---|---|---|---|
| calculated | 54.67 | 10.14 | 6.71 | 16.99 |
| found | 53.05 | 9.96 | 6.46 | 17.71 |
| $^1$H-NMR: | t(4H)4.22; m(4H)3.71; m(4H)3.20; m (20H)2.10; m(24H)1.31. | | | |
| $^{13}$C-NMR: | 158.17; 68.38(2C); 58.08(4C); 47.17(2C); 29.10(2C); 20.67(4C); 19.11(4C). | | | |

EXAMPLE 35

Di-5-(N,N-diisopropylamino)pentyl carbonate dihydrochloride

A] A solution of diisopropylamine (51.6 ml, 0,368 mole) in dichloromethane (200 ml) was added to a suspension of glutaric anhydride (20 g, 0,175 mole) in dichloromethane (200 ml). The reaction mixture was refluxed for 6 hours, then cooled to room temperature and washed with 1N HCl (2×200 ml), anhydrified over sodium sulfate and evaporated to dryness thus yielding 37.7 g of crude N,N-diisopropyl-glutaryl-monoamide which was directly used in the next step.

B] A solution of the compound under B] (30.2 g, 0.14 mole) in THF (200 ml) was slowly dropped into a refluxed suspension of lithium aluminium hydride (21 g, 0.561 mole) in THF (300 ml). At the end of the addition the-reaction mixture was refluxed for 30 minutes, then cooled to room temperature and stirred overnight, then added with a mixture of THF (66 ml) and water (8.5 ml), followed by a 20% solution of sodium hydroxide (22 ml). The aqueous phase was alkalinized with a 32% solution of sodium hydroxide and extracted with chloroform (3×200 ml). The organic phase was anhydrified over sodium sulfate and evaporated to provide 22.3 g of 5-(N,N-diisopropylamino)pentanol (yield: 85%) which was used as such in the next step.

C] A solution of the compound under B] (7 g, 37.4 mmoles) in dichloromethane (20 ml) was added with metallic sodium (86 mg, 3.7 mmoles), then a solution of CDI (3 g, 18.7 mmoles) in dichloromethane (40 ml) was dropped therein at room temperature. The reaction mixture was stirred overnight. The remaining solid was filtered off and the organic phase was washed with water (2×40 ml), then with 0,03M HCl (8×25 ml) and anhydrified over soldium sulfate, ane the solvent was evaporated thus providing 5.6 g of di-5-(N,N-diisopropylamino)pentyl carbonate.

| Elemental analysis: | C | H | N |
|---|---|---|---|
| calculated | 68.95 | 12.08 | 6.99 |
| found | 79.00 | 12.50 | 6.85 |

| | |
|---|---|
| $^1$H-NMR: | m(4H)4.12; m(4H)2.99; m(4H)2.37; m(4H)1.68; m(8H)1.51÷1.28; d(24H)0.99. |
| $^{13}$C-NMR: | 155.54; 68.00(2C); 55.34(4C); 47.71(2C); 35.30(2C); 26.91(2C); 24.91(2C); 21.39 (8C). |

D] The compound under C] was dissolved in chloroform (100 ml) and added with an ether solution of 2N HCl (14 ml, 28 mmoles). The solution was evaporated under vacuum and the resulting solid was taken up 3 times in ethyl ether and evaporated again to dryness thus yielding 7 g of the title product as an oil (yield: 81%).

| Elemental analysis: | C | H | N | Cl |
|---|---|---|---|---|
| calculated | 58.33 | 10.64 | 5.92 | 14.97 |
| found | 57.41 | 10.39 | 5.07 | 13.50 |

| | |
|---|---|
| $^1$H-NMR: | m(1H)4.14; m(4H)3.67; m(4H)3.07; m(12H)1.80÷1.34; d(24H)1.29. |
| $^{13}$C-NMR: | 158.91; 71.18(2C); 57.80(4C); 50.17(2C); 30.19(2C); 29.67(2C); 25.30(2C); 20.67 (4C); 19.07(4C). |

EXAMPLE 36

5-(N,N-diisopropylamino)pentyl-3-(N,N-diisopropylamino)propyl carbonate dihydrochloride A] CDI (2.2 g, 13.5 mmoles) was added to a solution of the compound of Example 34,B] (1.95 g, 12 mmoles) in chloroform (25 ml) and the reaction mixture was stirred at room temperature for 4 hours. The the organic phase was washed with water (25 ml), anhydrified over sodium sulfate, and the solvent was evaporated under vacuum. The crude was dissolved in THF (25 ml) and the resulting solution was added to a solution of the compound of Example 35,C] (2.5 g, 13.5 mmoles) in THF (25 ml) previously treated with a 1.6M solution of butyl lithium (2.5 ml, 13.5 mmoles). The reaction mixture was stirred overnight at room temperature, then the solvent was removed under vacuum. The crude was dissolved in chloroform (50 ml) and the solution was washed with water (2×25 ml), with 0.03N HCl (6×15 ml) and anhydrified over sodium sulfate. The solvent was evaporated under vacuum and the resulting crude was purified by flesh chromatography (eluent: n-hexane/ethyl acetate 3:7) yielding 1.15 g of 5-(N,N-diisopropylamino)-pentyl-3-(N,N-diisopropylamino)propyl carbonate.

| Elemental analysis: | C | H | N |
|---|---|---|---|
| calculated | 67.70 | 11.90 | 7.52 |
| found | 67.10 | 11.82 | 7.27 |

| | |
|---|---|
| $^1$H-NMR: | m(2H)4.17; m(2H)4.12; m(4H)2.98; m(2H)2.36; m(2H)1.73; m(2H)1.67; m(4H)1.49÷1.26; d(24H)0.98. |
| $^{13}$C-NMR: | 155.54; 68.12; 66.48; 48.55(2C); 48.16(2C); 45.21; 41.05; 31.27; 29.70; 28.87; 23.66; 20.82(8C). |

B] The compound under A] was dissolved in ethyl ether (25 ml) and added with an ether solution of 2N HCl (3 ml, 6.2 mmoles). The solvent was evaporated under vacuum and the resulting solid was dissolved in ethyl ether and evaporated 3 times giving 1.35 g of the title product (yield: 50%).

| Elemental anaylsis: | C | H | N | Cl |
|---|---|---|---|---|
| calculated | 56.62 | 10.41 | 6.29 | 15.92 |
| found | 53.52 | 10.38 | 5.73 | 16.82 |

| | |
|---|---|
| $^1$H-NMR: | m(2H)4.20; m(2H)4.15; m(4H)3.69; m(2H)3.20; m(2H)3.07; m(2H)2.10; m 84H)1.68; m(2H)1.42; d(12H)1.30; d(12H)1.29. |
| $^{13}$C-NMR: | 158.49; 71.46; 68.13; 58.10(2C); 57.81(2C); 50.17; 47.18; 30.21; 29.70; 29.28; 25.29; 20.71(4C); 19.10(4C). |

EXAMPLE 37

Di-[(N-butyl-piperid-3-yl)methyl carbonate dihydrochloride

A] A 1N solution of sodium hydroxide (174 ml, 0.17 mole) was added to a mixture of 3-piperidinemethanol (20 g, 0.17 mole) and butyl bromide (23 ml, 0.2 mole) in ethanol (200 ml). The reaction mixture was refluxed for 4 hours, then the solvent was evaporated under vacuum. The aqueous solution was acidified with HCl and washed with ethyl ether, then treated with a 32% solution of sodium hydroxide to pH-12 and extracted with ethyl ether. The combined organic phases were anhydrified over sodium sulfate and the solvent was evaporated under vacuum. The crude was purified by distillation yielding 23 g of N-butyl-3-piperidinemethanol (b.p.: 115–117/6 mmHg) (yield: 79%).

B] CDI (8.14 g, 50 mmoles) was added to a solution of the compound under A] (6.6 g, 50 mmoles) in dichloromethane (100 ml) and the reaction mixture was stirred for 4 hours at room temperature, then the solution was added to a suspension of sodium salt prepared from the compound under A] (8.6 g, 50 mmoles) and a 80, suspension of sodium hydride (1.5 g, 50 mmoles) in THF (25 ml). The reaction mixture was stirred overnight at room temperature, then the solvents were removed under vacuum, and the resulting crude was dissolved in dichloromethane (100 ml) and the solution was washed with water (2×100 ml), with 0.03N HCl (6×100 ml) and anhydrified over sodium sulfate. The solvent was evaporated under vacuum yielding 10.9 g of di-[(N-butyl-piperid-3-yl)methyl carbonate.

| Elemental analysis: | C | H | N |
|---|---|---|---|
| calculated | 68.44 | 10.94 | 7.60 |
| found | 69.66 | 11.38 | 7.51 |

| | |
|---|---|
| $^1$H-NMR: | m(4H)4.00; m(2H)2.89; m(2H)2.80; 2(4H)2.30; m(20H)2.10 ÷ 1.21; m(2H)1.01; t(6H)0.91. |
| $^{13}$C-NMR | 155.52; 71.01(2C); 59.15(2C); 57.12(2C); 54.31(2C); 36.00(2C); 29.24(2C); 27.34 (2C); 24.86(2C); 20.98(2C); 14.21(2C). |

C] The compound under B] was dissolved in ethyl ether (200 ml) and added with an ether solution of 2N HCl (29.6 ml, 51.9 mmoles). The solvent was evaporated under vacuum and the solid was dissolved in chloroform and evaporated 3 times, then tritured with ethyl ether giving 5.6 g of the title product as a white solid (yield: 25%) (m.p.: 197°–199° C.).

| Elemental analysis: | C | H | N | Cl |
|---|---|---|---|---|
| calculated | 57.13 | 9.59 | 6.35 | 16.06 |
| found | 55.87 | 9.49 | 6.22 | 15.72 |

$^1$H-NMR: m(4H)4.10; m(4H)3.55; m(4H)3.08; m(4H) 2.91 ÷ 2.64; m(2H)2.20; m(10H)2.05 ÷ 1.59; m (6H)1.42 ÷ 1.19; t(6H)0.88.
$^{13}$C-NMR: 163.21; 72.28(2C); 60.33(2C); 57.14(2C); 55.67(2C); 36.90(2C); 28.29(2C); 26.90 (2C); 25.12(2C); 22.19(2C); 15.67(2C).

EXAMPLE 38

Di-[6-(N,N-dibutylamino)hex-3-yl] carbonate dihydrochloride hydrate

A] Ethyl vinyl ketone (25 g, 0,297 mole) was slowly added to a solution of nitromethane (80 ml, 1.48 mole) and 1,1,3,3-tetramethylguanidine (3.7 ml, 0.029 mole) in acetonitrile (180 ml) while maintaining the room temperature by cooling with ice. The reaction mixture was stirred for 48 hours at room temperature, then added with water (70 ml), and the pH was corrected to 5 by acetic acid. The solvent was evaporated under vacuum and the aqueous phase was extracted with ethyl acetate (2×100 ml). The combined organic phases were washed with chilled water (100 ml) and anhydrified over sodium sulfate, then the solvent was evaporated under vacuum to give 42 g of crude 6-nitrohexan-3-one which was used as such in the next step.

B] Sodium borohydride (5 g, 0,132 mole) was added to a solution of the compound under A] (43 g, 0.23 mole) in ethanol (340 ml), at room temperature. The reaction mixture was stirred for 2 hours, then acidified with concentrated HCl, the salts were filtered off the the filtrate was evaporated to give ;27 g of crude 6-nitrohexan-3-ol which was used as such in the next step.

C] A mixture of the compound under B] (20 g, 0.196 mole) and platinum oxide 8300 mg) in methanol (200 ml) was hydrogenated under pressure (30 p.s.i.) at room temperature, then the catalyst was filtered off and the solvent was evaporated under vacuum. The resulting crude was purified by distillation to give 4 g of 6-aminohexan-3-ol (yield: 17%) (b.p.: 104°–106° C./10 mmHg).

D] A 32% solution of sodium hydroxide (6.3 ml, 68 mmoles) was added to a mixture of the compound under C] (4 g, 34 mmoles) and butyl bromide (7.6 ml, 68 mmoles) in ethanol (40 ml). Such mixture was refluxed for 24 hours, then the solvent was evaporated under vacuum. The aqueous solution was acidified with HCl and washed with ethyl ether, then treated with a 32% solution of sodium hydroxide until pH-12, and extracted with ethyl ether. The combined organic phases were anhydrified over sodium sulfate, and the solvent was evaporated under vacuum. The resulting crude was purified by flash chromatography (eluent: chloroform/methanol/concentrated ammonia 15:1:0.3) yielding 2.4 g of 6-(N,N-dibutylamino)hexan-3-ol (yield: 31%).

E] CDI (0.85 g, 5.2 mmoles) was added to a solution of the compound under D] (1.2 g, 5.2 mmoles) in THF (25 ml), and the reaction mixture was stirred for 4 hours at room temperature, then was added to a suspension of sodium salt prepared from the compound under D] (1.2 g, 5.2 mmoles) and a 80% suspension of sodium hydride (125 mg, 5.2 mmoles) in THF (25 ml). The reaction mixture was refluxed for 4 hours, then the solvent was evaporated under vacuum. The crude was dissolved in ethyl ether (100 ml) and the solution was washed with water (2×20 ml), with 0.03 HCl (6×20 ml) and anhydrified over sodium sulfate. The solvent was evaporated under vacuum yielding 1.4 g of di-[6-(N,N-dibutylamino)hex-3-yl] carbonate.

| Elemental analysis: | C | H | N |
|---|---|---|---|
| calculated | 71.85 | 12.47 | 5.78 |
| found | 72.25 | 12.78 | 6.17 |

$^1$H-NMR: m(2H)4.67; m(12H)2.44 ÷ 2.35; m(28H) 1.71 ÷ 1.20; t(6H)0.94; t(12H)0.92.
$^{13}$C-NMR: 155.47; 79.67(2C); 53.99(6C); 31.78(2C); 29.48(4C); 27.33; 27.23; 23.04(2C); 22.91 (4C); 14.25(4C); 9.69(2C).

F] The compound under E] was dissolved in chloroform (100 ml) and added with an ether solution of 2N HCl (2.88 ml, 5.761 mmoles). The solvent was evaporated under vacuum and the resulting crude was dissolved in chloroform and evaporated 3 times, then tritured with ethyl ether thus yielding 1.2 g of the title product (yield: 22%).

| Elemental analysis: | C | H | N | Cl |
|---|---|---|---|---|
| calculated | 60.50 | 11.20 | 4.87 | 12.32 |
| found | 59.36 | 11.01 | 4.95 | 12.31 |

$^1$H-NMR: m(2H)4.71; m(12H)3.19 ÷ 3.07; m(20H) 1.76 ÷ 1.59; m(8H)1.35; t(12H)0.91; t(6H) 0.89.
$^{13}$C-NMR: 158.64(0.5C); 158.42(0.5C); 83.45; 83.37; 55.69(4C); 55.17; 55.01; 32.77; 32.63; 29.45; 29.17; 28.14(4C); 22.21(5C); 22.11; 15.73(4C); 11.73; 11.54.

EXAMPLE 39

Di-[2-(N-butyl-2-piperid-2-yl)ethyl] carbonate dihydrochloride hydrate

A] A solution of 1N sodium hydroxide (156 ml, 0.156 mole) was added to a mixture of 2-piperidine-ethanol (20 ml, 0.156 mole) and butyl bromide (21 ml, 0.187 mole) in ethanol (200 ml). The reaction mixture was refluxed for 4 hours, then the solvent was evaporated under vacuum. The aqueous solution was acidified with HCl and washed with ethyl ether, then it was treated with a 32% solution of sodium hydroxide until pH-12 and extracted with ethyl ether. The combined organic phases were anhydrified over sodium sulfate and the solvent was evaporated under vacuum. The resulting crude was purified by distillation yielding 1.7 g of N-butyl-2-piperidine-ethanol (b.p.: 88°–99° C./0mmHg) (yield: 40%).

B] CDI (2.9 g, 18 mmoles) was added to a solution of the compound under A] (3.3 g, 18 mmoles) in THF (50 ml) and the mixture was stirred for 4 hours at room temperature, then it was added to a suspension of sodium salt prepared from the compound under A] (3.3 g, 18 mmoles) and a 80% suspension of sodium hydroxide (540 mg, 18 mmoles) in THF (50 ml). The mixture was refluxed for 2 hours, then the solvent was evaporated under vacuum. The crude was dissolved in ethyl ether (100 ml) and the solution was washed with water (2×70 ml), with 0.03N HCl (6×80 ml) and anhydrified over sodium sulfate. The solvent was evaporated under vacuum and the resulting crude was purified by flash chromatography (eluent: chloroform/methanol/ concentrated ammonia 15:1:0.3) yielding 2 g of di-[2-(N-butyl-2-piperid-2-yl)-ethyl] carbonate.

| Elemental analysis: | C | H | N |
|---|---|---|---|
| calculated | 69.65 | 11.19 | 7.06 |
| found | 69.67 | 11.00 | 7.03 |
| $^1$H-NMR: | m(4H)4.27 ÷ 4.06; m(1H)2.82; m(1H)2.76; m(2H)2.66 ÷ 2.52; m(6H)2.45 ÷ 2.14; m(2H)2.04 ÷ 1.87; m(22H)1.82 ÷ 1.16; t(6H)0.89. | | |
| $^{13}$C-NMR: | 155.37; 65.88(2C); 57.03(2C); 53.34(2C); 51.49(2C); 30.40(2C); 29.98(2C); 28.41(2C); 25.33(2C); 23.34(2C); 20.98(2C); 14.23(2C). | | |

C] The compound under B] was dissolved in ethyl ether (30 ml) and added with a ether solution of 2N HCl (5 ml, 10 mmoles). The solvent was evaporated under vacuum, and the resulting solid was dissolved in chloroform and evaporated 3 timer, then tritured with ethyl ether yielding 1.5 g of the title product as a white solid (yield: 18%).

| Elemental anaiysis: | C | H | N | Cl |
|---|---|---|---|---|
| calculated | 56.66 | 9.92 | 5.75 | 14.54 |
| found | 55.96 | 10.21 | 5.49 | 14.02 |
| $^1$H-NMR: | m(4H)4.38 ÷ 4.05; m(10H)3.58 + 3.22; m(20H)2.43 ÷ 1.50; m(4H)1.35; t(6H)0.91. | | | |
| $^{13}$C-NMR: | 154.48; 64.16 + 63.99(2C); 59.91 + 58.14 + 57.92(2C); 52.81 + 52.45(2C); 48.92 + 48.23 + 47.90(2C); 29.47; 27.52 + 27.36 + 26.88 + 26.21(2C); 24.62; 24.49(2C); 22.95 + 22.64 + 22.44 + 22.04(2C); 20,35 + 20.17 + 20.00 + 19.89 + 19.75(4C); 13.70(2C). | | | |

EXAMPLE 40

Di-[(S)-5-(N-dibutylammino)pent-2-yl] carbonate dihydrochloride hydrate

A] Platinum oxide (47 mg) was added to a solution of (S)-5-nitro-2-pentanol (Nakamura K. et al., Tetrahedron Letters, 46, 7471–7481, 1990) (4.7 g, 35 mmoles) in ethanol (30 ml) and the reaction mixture was hydrogenated at 30 p.s.i. at room temperature, then the catalyst was filtered off and the solvent was evaporated under vacuum yielding 3.4 g of crude (S)-5-amino-2-pentanol (yield: 94%) which was used as such in the next step.

B] A solution of 1N sodium hydroxide (22 ml, 44 mmoles) was added to a mixture of the compound under A] (2.7 g, 22 mmoles) and butyl bromide (5 ml, 46 mmoles) in ethanol (50 ml). The reaction mixture was heated to reflux for 4 hours, then the solvent was removed under vacuum. The aqueous solution was acidified hy HCl and washed with ethyl ether, then treated with a 32% solution of sodium hydroxide to pH-12 and extracted with ethyl ether. The organic phases were anhydrified over sodium sulfate and the solvent was evaporated under vacuum. The resulting crude was purified by flash chromatography (eluent: chloroform/methanol/concentrated ammonia 10:1:0.1) yielding 1.6 g of pure (S)-5-(N,N-dibutylamino)-2-pentanol (yield: 30%).

C] CDI (0.59 g, 3.6 mmoles) was added to a solution of the compound under B] (0.8 g, 3.6 mmoles) in THF (15 ml), and the reaction mixture was stirred for 4 hours at room temperature, then added to a suspension of sodium salt prepared from the compound under B] (0.8 g, 3.6 mmoles) and a 80% suspension of sodium hydroxide (109 mg, 3.6 mmoles) in THF (15 ml). The reaction mixture was refluxed for 4 hours, then the solvent was evaporated under vacuum. the resulting crude was dissolved in ethyl ether (50 ml) and the solution was washed with water (2×10 ml) and with 0.03N HCl (6×10 ml), then anhydrified over sodium sulfate. The solvent was evaporated under vacuum and the crude was purified by flash chromatography (eluent: chloroform/methanol 9:1) yielding 950 mg of di-[(S)-5-(N-dibutylamino)pent-2-yl] carbonate.

| Elemental analysis: | C | H | N |
|---|---|---|---|
| calculated | 71.00 | 12.36 | 6.13 |
| found | 65.50 | 11.25 | 5.90 |
| $^1$H-NMR: | m(2H)4.76; m(12H)2.37; m(24H)1.67 ÷ 1.19; d(6H)1.27; t(12H)0,93. | | |
| $^{13}$C-NMR: | 154.74; 75.01(2C); 54.01(6C); 34.01(2C); 29.41(4C); 23.17(2C); 20.90(4C); 20.13(2C); 14.25(4C). | | |

D] The compound under B] was dissolved in chloroform (10 ml) and added with an ether solution of 2N HCl (2 ml, 4 mmoles). The solvent was evaporated under vacuum and the resulting solid was dissolved in chloroform and evaporated 3 times, then tritured with ethyl ether giving 1.1 g of the title compound as an oil (yield: 58%).

| Elemental analysis: | C | H | N | Cl |
|---|---|---|---|---|
| calculated | 59.21 | 11.04 | 5.11 | 12.95 |
| found | 58.87 | 11.20 | 5.55 | 10.34 |
| $^1$H-NMR: | m(2H)4.80; m(12H)3.12; m(16H)1.56 ÷ 1.81; m(8H)1.35; d(6H)1.27; t(12H)0.91. | | | |
| $^{13}$C-NMR: | 157.77; 78.51(2C); 55.67(4C); 55.12(2C); 34.70(2C); 28.12(4C); 22.19(6C); 21.88(2C); 15.71(4C). | | | |

EXAMPLE 41

Di-[(N-butylpirrolid-3-yl)methyl] carbonate dihydrochloride monohydrate

A] A 32% solution of sodium hydroxide (123 ml) was added to a mixture of glycin (50 g, 0.66 mole) and butyl bromide (75 ml, 0.66 mole) in methanol (600 ml) and water (600 ml), the reaction mixture was refluxed for 24 hours, then the solvend was evaporated under vacuum. The crude was dissolved in ethanol, the salts were filtered off 3 times, and the solvent was evaporated under vacuum. The resulting crude was purified by flash chromatography (eluent: chloroform/methanol/concentrated ammonia 6:4:0.5) yielding 36 g of N-butyl-glycine.

B] Methyl acrilate (30 ml, 0.33 mole) was added to a suspension of the compound under A] (36 g, 0.27 mole), paraformaldehyde (9.9 g, 0.33 mole) and magnesium sulfate (63 g, 0.52 mole) in toluene (500 ml). The reaction mixture was refluxed for 2 hours, then the organic phase was extracted with a solution of 1N HCl (400 ml). The aqueous solution was treated with sodium hydrocarbonate until pH-8 amd extracted with ethyl ether (5×150 ml). The combined organic phases were anhydrified over sodium sulfate and the solvent was evaporated under vacuum to yield 10.6 g of crude N-butylpirrolidine-3-carboxylate methyl ester (yield: 21%) which was used as such in the next step.

C] A solution of the compound under B] (10.6 g, 54 mmoles) in THF (30 ml) was slowly added to a suspension of lithium aluminium hydride (2.3 g, 60 mmoles) in THF (100 ml) at 0° C. These mixture was stirred for 1 hour at room temperature, added with a mixture of THF (7 ml) and water (1 ml), then with 32% sodium hydroxide (2.3 ml) and water (9 ml). The formed salts were filtered off and the filtrate was evaporated under vacuum yielding 7.4 g of crude N-butyl-3-pirrolidine-methanol (yield: 87%) which was used as such in the next step.

D] CDI (3.7 g, 23 mmoles) was added to a solution of the compound under C] (3.6 g, 23 mmoles) in THF (75 ml), and the reaction mixture was stirred for 4 hours at room temperature. The solution was then added to a suspension of sodium salt prepared form the compound under C] (3.6 g, 23 mmoles) and a 80% suspension of sodium hydride (680 mg, 23 mmoles) in THF (75 ml). The reaction mixture was refluxed for 4 hours, then the solvent was evaporated under vacuum. The crude was dissolved in ethyl ether (100 ml) and the solution was washed with water (2×50 ml) and 0.03N HCl (6×50 ml), and anhydrified over sodium sulfate. The solvent was evaporated under vacuum to give 3.6 g of di-[(N-butylpirrolid-3-yl) methyl] carbonate.

| Elemental analysis: | C | H | N |
|---|---|---|---|
| calculated | 67.02 | 10.66 | 8.23 |
| found | 66.39 | 11.41 | 8.01 |

| $^1$H-NMR: | m(4H)4.03; (16H)2.70 ÷ 2.21; m(2H) 2.04 ÷ 1.86; m(10H)1.53 ÷ 1.20; t(6H)0.88. |
|---|---|
| $^{13}$C-NMR: | 155.34; 71.16(2C); 57.32(2C); 56.28(2C); 53.93(2C); 36.45(2C); 31.17(2C); 27.28 (2C); 20.92(2C); 14.18(2C). |

E] The compound under D] was dissolved in chloroform (180 ml) and added with an ether solution of 2N HCl (10.5 ml, 21 mmoles). The solvent was evaporated under vacuum and the resulting solid was dissolved in chloroform, evaporated 3 times and tritured with ethyl ether to yield 3.5 g of the title product as an oil (yield: 87%).

| Elemental analysis: | C | H | N | Cl |
|---|---|---|---|---|
| calculated | 52.89 | 9.34 | 6.49 | 16.43 |
| found | 52.69 | 9.54 | 6.35 | 15.99 |

| $^1$H-NMR: | m(4H)4.19; m(14H)3.87 ÷ 2.77; m(2H)2.23; m(2H)1.88; m(4H)1.65; m(4H)1.34; t(6H) 0.88. |
|---|---|
| $^{13}$C-NMR: | 158.10; 71.50(2C); 58.34(2C); 58.00(2C); 56.67(2C); 38.31(2C); 30.11(2C); 28.54 (2C); 22.06(2C); 15.64(2C). |

EXAMPLE 42

Di-5-(N-phenyl-N-ethyl)-pent-2-yl-carbonate dihydrochloride hydrate

A] Starting from levulinic acid (13.2 ml, 130 mmoles) and ethylaniline (18.1 ml, 155 mmoles), and substantially applying the procedure of Example 10,A–B], 5.8 g of di-5-(N-phenyl-N-ethyl)-pent-2-yl-carbonate were obtained.

| Elemental analysis: | C | H | N |
|---|---|---|---|
| calculated | 73.60 | 9.15 | 6.36 |
| found | 73.60 | 9.20 | 6.34 |

| $^1$H-NMR: | m(4H)7.23; m(6H)6.72 ÷ 6.63; m(2H)4.81; q (2H)3.38; q(2H)3.36; m(4H)3.28; m(8H) 1.66; d(3H)1.32; d(3H)1.31; t(3H)1.16; t(3H)1.15. |
|---|---|
| $^{13}$C-NMR: | 154.70; 148.00(2C); 129.44(4C); 115.72 (2C); 112.07(4C); 74.94(2C); 50.21(2C); 45.09(2C); 33.56(2C); 23.65(2C); 20.22 (2C); 12.42(2C) |

B] Starting from the compound under A] and substantially applying the procedure of Example 1,E] to yield, the title product was obtained.

| Elemental analysis: | C | H | N |
|---|---|---|---|
| calculated | 61.01 | 8.34 | 5.27 |
| found | 53.52 | 9.56 | 5.61 |

| $^1$H-NMR: | m(10H)7.62 ÷ 7.41(2H)4.50; m (8H)3.65 ÷ 3.50; m(8H)1.55 ÷ 1.13; d(3H) 1.07; t(3H)1.05; t(3H)1.04. |
|---|---|
| $^{13}$C-NMR: | 157.41; 139.45(2C); 133.57(6C); 124.94 (4C); 78.16(2C); 60.29(2C); 57.47; 57.36; 34.45; 34.38; 23.37(2C); 21.70(2C); 12.49. |

EXAMPLE 43

Di-3-(N,N-dibutylamino)-benzyl carbonate dihydrochloride hydrate

A] Starting from 3-amino-benzil alcohol (13 g, 0.105 mole), butyl-bromide (39 ml, 0.34 mole) and 1N sodium hydroxide (300 ml) and following the procedure of Example 40,B], there were obtained 8.8 g of 3-dibutylamino-benzyl alcohol (yield: 36%).

B] Using the compound under A] (8.5 g, 36 mmoles), CDI (2.9 g, 18 mmoles) and 80% sodium hydride (540 mg, 18 mmoles), and following the procedure of Example 40,C], there were obtained 2.2 g of di-3-(N,N-dibutylamino)-benzyl carbonate (yield: 25%).

| Elemental analysis: | C | H | N |
|---|---|---|---|
| calculated | 74.96 | 9.74 | 5.64 |
| found | 74.31 | 9.43 | 5.69 |

| $^1$H-NMR: | t(2H)7.19; m(6H)6.63; s(4H)5.12; m(8H) 3.26; m(8H)1.64 ÷ 1.49; m(8H)1.36; t(12H) 0.96. |
|---|---|
| $^{13}$C-NMR: | 155.48; 148.52(2C); 136.35(2C); 129.53 (2C); 115.13(2C); 111.90(2C); 111.58(2C); 70.56(2C); 50.88(4C); 29.52(4C); 20.50 (4C); 14.17(4C). |

C] The compound under B] (2.2 g, 4.4 mmoles) dissolved in 20 ml of ethyl ether was added with 4.4 ml (8.8 mmoles) of an ether solution of 2N HCl was added. The solvent was evaporated and the crude was dissolved in chloroform and evaporated three times thus yielding 2.4 g of the title product.

| Elemental analysis: | C | H | N | Cl |
|---|---|---|---|---|
| calculated | 63.36 | 8.92 | 4.77 | 12.07 |
| found | 62.73 | 8.64 | 4.67 | 11.78 |

$^1$H-NMR: m(8H)7.62 ÷ 7.44; s(4H)5.23; m(8H)3.53; m(16H)1.43 ÷ 1.09; t(12H)0.73.
$^{13}$C-NMR: 157.92; 140.96(2C); 140.47(2C); 133.93 (2C); 132.77(2C); 125.24(2C); 124.32(2C); 71.90(2C); 61.47(4C); 29.39(4C); 21.87 (4C); 15.59(4C).

EXAMPLE 44

Di-4-(N,N-dibutylaminomethyl)benzyl carbonate dihydrochloride

A] 4-(Aminomethyl)benzoic acid (20 g, 0.132 mole) was added to a suspension of lithium aluminium hydride (5.5 g, 0,145 moles) in 300 ml of THF, at room temperature. The suspension was refluxed for 4 hours, the cooled to room temperature and added with, successively, a mixture THF/water 7:1 (32 ml), 32% sodium hydroxide (10 ml) and water (40 ml). The formed solid was filtered off and the solvent evaporated under vacuum to provide 7 g of 4-(aminomethyl)benzyl alcohol che was directly used in the next step.

B] Starting from the compound under A] (7 g, 50 mmoles) butyl bromide (12 ml, 110 mmoles) and 1N sodium hydroxide (110 ml) and substantially following the procedure of Example 40,B], there were obtained 2.2 g of 4-(dibutylamino)benzyl alcohol (yield: 18%).

C] Starting from the compound under B] (2.1 g, 8.4 mmoles), CDI (680 mg, 4.2 mmoles) and 80% sodium hydride (126 mg, 4.2 mmoles) and substantially following the procedure of Example 40,C], there were obtained 890 mg of di-4-(N,N-dibutylaminomethyl)benzyl carbonate (yield: 40%).

| Elemental analysis: | C | H | N |
|---|---|---|---|
| calculated | 75.53 | 9.99 | 5.34 |
| found | 76.32 | 9.89 | 5.26 |

$^1$H-NMR: s(8H)7.32; s(4H)5.16; s(4H)3.53; m(H) 2.39; m(16H)1.51 ÷ 1.19; t(12H)0.87.
$^{13}$C-NMR: 155.27; 141.11(2C); 133.53(2C); 129.06 (4C); 128.41(4C); 69.85(2C); 58.4(2C); 53.70(4C); 29.39(4C); 20.76(4C); 14.26 (4C).

D] The compound under C] (700 mg, 1.4 mmoles) was dissolved in ethyl ether (10 ml), and an ether solution of 2N hydrochloric acid (1.4 ml, 2.8 mmoles) was added therein. The solvent was evaporated off and the resulting crude was dissolved in chloroform and evaporated three times thus yielding 690 mg of the title product.

| Elemental analysis: | C | H | N | Cl |
|---|---|---|---|---|
| calculated | 66.31 | 9.11 | 4.69 | 11.86 |
| found | 66.56 | 9.19 | 4.61 | 11.79 |

$^1$H-NMR: m(8H)7.42; s(4H)5.14; s(4H)4.27; m(8H) 3.03; m(8H)1.61; m(8H)1.24; t(12H)0.81.

$^{13}$C-NMR: 158.17; 139.81(2C); 134.13(4C); 132.51 (2C); 131.68(4C); 75.33(2C); 59.36(2C) 55.18(4C); 27.93(4C); 22.11(4C); 15.60 (4C).

EXAMPLE 45

Di-1-(N,N-dibutylamino)4-dodecyl carbonate dihydrochloride

A] A solution of 4-aminobutyraldehyde diethylacetale (90 ml, 0.5 mole) and butyl bromide (121 ml, 1.1 mole) in ethanol (1.000 ml) was added with a 1N solution of sodium hydroxide (1.130 ml). The reaction mixture was refluxed for 8 hours. The reaction solvent was evaporated off and the aqueous solution was extracted with diethyl ether. The organic phases were combined and anhydrified over sodium sulfate, then evaporated under vacuum. The resulting crude was purified by fractionated distillation to yield 54 g of 4-dibutylaminobutyraldehyde diethylacetale (yield: 39%). B.p.: 95°–06° C. (0,05 mmHg).

$^1$H-NMR: t (1H) 4.49; m (4H) 3.70–3.40; m (6H) 2.38; m (12H) 1.65–1.20; t (6H) 1.19; t (6H) 0.89.

B] A solution of the compound under A] (15 g, 55 mmoles) in 1N HCl (150 ml) was stirred at room temperature for 2 hours, then neutralized with a 1N solution of sodium hydroxide (150 ml) and extracted with methylene chloride. The organic phase was anhydrified over soldium sulfate, and the solvent evaporated under vacuum to yield 11 g of dibutylaminobutyraldehyde which was used as such in the next step (quantitative yield).

$^1$H-NMR: t (1H) 9.73; m (8H) 2.39; m (2H) 1.75; m (8H) 1.32; t (6H) 0.89.

C] A 2M solution of octylmagnesium bromide in THF (27 ml, 55 mmoles) was slowly added with a solution of the compound under B] (11 g, 55 mmoles) in diethyl ether (200 ml), at –15° C. under nitrogen. The reaction mixture was stirred for 1 hour at the same temperature, then at room temperature for a further hour. The solution was then poured in water (200 ml) and 1N HCl (60 ml). The phases were separated and the aqueous one extracted with diethyl ether. The organic phases were combined and anhydrified over sodium sulfate, and the solvent was evaporated under vacuum. The resulting crude was purified by silica gel chromatography (eluent: chloroform/methanol/ammonia 20:1:0.03) yielding 6.4 g of 1-(N,N-dibutylamino)-4-dodecanol (yield: 37%).

$^1$H-NMR: m (1H) 3.46; m (6H) 2.43; m (26H) 1.82–1.18; m (9H) 0.90.

D] CDI (1.6 g, 10 mmoles) was added to a solution of the compound under C] (3.1 g, 10 mmoles) in THF (100 ml), and the reaction mixture was refluxed for 4 hours. The solvent was stripped under vacuum and the correspondinf imidazolide was purified by silica gel column chromatography (eluent: chloroform/methanol/ammonia 20:1:0.03) yielding 3.2 g of a compound which was used as such in the next step.

$^1$H-NMR: s (1H) 8.12; s (1H) 7.41; s (1H) 7.08; m (1H) 5.08; m (6H) 2.40; m (4H) 1.70; m (22H) 1.62–1.15; m (9H) 0.89.

E] A 2M solution of butyl lithium in hexane (4 ml, 8 mmoles) was added to a solution of the compound under C] (2.3 g, 7.3 mmoles) in THF (50 ml), at –15° C., and the reaction mixture was stirred at such temperature for 30 minutes, then at room temperature for 1 hour. A solution of the compound under D] (3.2 g, 8 mmoles) in THF (30 ml) was added, and the reaction mixture was stirred at room temperature overnight. The solvent was evaporated and the resulting crude was purified by silica gel chromatography (eluent: toluene/ethanol/ammonia 30:1.3:0.1) yielding 0.8 g of di-1-(N,N-dibutylamino)4-dodecyl carbonate (yield: 17%).

| Elemental analysis; | C | H | N |
|---|---|---|---|
| calculated | 75.40 | 12.96 | 4.29 |
| found | 74.65 | 12.70 | 4.26 |

| $^1$H-NMR: | m(2H)4.70; m(12H)2.33 ÷ 2.43; m(52H) 1.19 ÷ 1.74; t(12H)0.91; t(6H)0.88. |
|---|---|
| $^{13}$C-NMR: | 155.35; 78.55(2C); 53.99(6C); 34.37 (2); 32.26(2); 32.02(2C); 29.67(4C); 29.45(5C); 29.40(3C); 25.41; 22.99; 22.81 (2C); 20.91(4C); 14.27(6C). |

F] The compound under E] (700 mg, 1.1 mmoles) was dissolved in ethyl ether (10 ml) and added with an ether solution of 2N HCl (1.1 ml, 2.2 mmoles). The solvent was evaporated and the resulting product was dissolved in chloroform and evaporated three times to yield 590 mg of the title product.

| Elemental analysis: | C | H | N | Cl |
|---|---|---|---|---|
| calculated | 67.83 | 11.94 | 3.86 | 9.77 |
| found | 66.63 | 11.10 | 4.03 | 10.52 |

| $^1$H-NMR: | m(2H)4.72; m(12H)3.11; m(52H)1.18 ÷ 1.77; t(12H)0.92; t(6H)0.83. |
|---|---|
| $^{13}$C-NMR: | 1.58.445; 80.63(2C); 55.71(4C); 54.65 (2C); 34.85(2C); 32.65(2C); 32.43(2C); 32.26(4C); 28.15(8C); 25.53(2C); 22.40 (4C); 22.28(2C); 16.97(2C); 16.02(4C). |

EXAMPLE 46

[4-(N,N-dibutylamino)butyl]-5-(N,N-dibutylamino)-2-methylpent-2-yl] carbonate dihydrochloride A] A 1.5M solution of methyl magnesium bromide in diethyl ether (104 ml, 157 mmoles) was lowly added to a solution of N,N-dibutyl-4-oxopentanamide (17 g, 75 mmoles) in anhydrous diethyl ether (450 ml) at 0° C. under nitrogen. The reaction mixture was stirred at 0° C. for 5 hours, then the solvent was evaporated under vacuum and the crude was dissolved in chloroform (500 ml) and washed with a 1N solution of HCl. The organic phase was anhydrified over sodium sulfate and evaporated.

The resulting crude was purified by silica gel chromatography (eluent: hexane/ethyl acetate 1:1) yielding 4.7 g (yield: 26%) of N,N-dibutyl-4-hydroxy-4-methyl-pentanamide.

$^1$H-NMR: m (4H) 3.28; t (2H) 2.45; t (2H) 1.82; m (8H) 1.63–1.20; m (6H) 1.21; t (3H) 0.94; t (3H) 0.90.

B] Lithium aluminium hydride (1.5 g, 38 mmoles) was added to a solution of the compound under A] (4.7 g, 19 mmoles) in THF (250 ml) at room temperature under nitrogen. The reaction mixture was stirred at room temperature for 3 hours, then cooled to 0° C. and added with THF/water 4:1 (10 ml), 1N sodium hydroxide (3 ml) and then water (11 ml). The formed salts were filtered off and the solvent evaporated under vacuum. The resulting crude was purified by silica gel chromatography (eluent: chloroform/methanol/ammonia 14:1:0.5) yielding 3.8 g of 5-(N,N-dibutylamino)-2-methyl-2-pentanol (yield: 78%).

$^1$H-NMR: m (6H) 2.40; m (2H) 1.59; m (10H) 1.51–1.10; s (6H) 1.16; t (6H) 0.89.

C] Starting from the compound under B] (1.8 g, 8 mmoles) and CDI (1.3 g, 8 mmoles) and substantially proceeding as in Example 45,D], there were obtained, after purification by chromatography, 1.23 g of the corresponding imidazolide (yield: 46%).

$^1$H-NMR: s (1H) 8.08; S (1H) 7.37; s (1H) 7.03; m (6H) 2.39; m (2H) 1.89; s (6H) 1.59; m (10H) 1.66–1.18; t (6H) 0.90

D] Starting from the compound of Example 20,B] (0.84 g, 4.2 mmoles), the compound under C] (1.2 g, 3.8 mmoles) and a 2N solution of butyl lithium (2.6 ml, 4.2 mmoles) and substantially proceeding as in Example 45,E], after purification by chromatography there were obtained 590 mg of [4-(N,N-dibutylamino)butyl]-5-(N,N-dibutylamino)-2-methyl pent-2-yl] carbonate (yield: 34%).

$^1$H-NMR: t (2H) 4.06; m (12H) 2.39; m (24H) 1.87–1.15; s (6H) 1.47; t (12H) 0.90

E] The compound under D] (1.3 g, 1.3 mmole) was dissolved in ethyl ether (50 ml) and added with an ether solution of 1N HCl (1.3 ml, 2.6 mmoles). The solvent was evaporated and the resulting product was dissolved in chloroform and evaporated three times thus yielding 670 mg of the title product.

| Elemental analysis: | C | H | N | Cl |
|---|---|---|---|---|
| calculated | 58.48 | 10.68 | 5.05 | 14.39 |
| found | 60.99 | 11.37 | 5.27 | 13.34 |

| $^1$H-NMR: | t(2H)4.09; m(12H)3.09; m(16H)1.54 ÷ 1.77; s(6H)1.43; m(8H)1.32; t(12H)0.88. |
|---|---|
| $^{13}$C-NMR: | 156.78; 88.05; 69.82; 55.56(4C); 55.32; 54.94; 39.41; 27.95(4C); 27.65(2C); 22.71; 22.19; 22.13(4C); 20.89; 15.65(4C). |

EXAMPLE 47

Di-5-(N-dodecyl-N-methyl)-2-pentyl carbonate dihydrochloride

A] A solution of ethyl chloroformate (17 ml, 178 mmoles) in methylene chloride (200 ml) was added to a solution of dodecylamine (30 g, 162 mmoles) and triethylamine (24 ml, 178 mmoles) in methylene chloride (250 ml) at −25° C. At the end of the addition, the reaction mixture was stirred at 0° C. for 2 hours, then the formed salts were filtered off and the organic phase was washed with 1N HCl, anhydrified over sodium sulfate and evaporated thus yielding 40 g of dodecylamino-ethyl-carbamate (yield: 96%).

$^1$H-NMR: bs (1H) 4.62; q (2H) 4.11; q (2H) 3.16; m (2H) 1.48; s (18H) 1.27; t (3H) 0.90.

B] A solution of the compound under A] (39.7 g, 154 mmoles) in THF (250 ml) was added to a suspension of lithium aluminium hydride (9.2 g, 231 mmoles) in THF (350 ml) at room temperature. The reaction mixture was refluxed for 2 hours, then THF/water 4:1 (32 ml), 20% sodium hydroxide (9 ml) and then water (37 ml) were added at 0° C. The formed salts were filtered off and the solvent evaporated under vacuum yielding 28 g of N-methyl-dodecylamine (yield: 91%).

$^1$H-NMR: t (2H) 2.58; s (3H) 2.45; m (2H) 1.50; s (18H) 1.30; t (3H) 0.90.

C] Starting from the compound under B] (28 g, 140 mmoles) and levulinic acid (13.6 g, 117 mmoles) and substantially proceeding as in Example10,A], after purification there were obtained 21.5 g of N-methyl-N-dodecyl-4-oxopentanamide (yield: 62%).

$^1$H-NMR: m (2H) 3.31; s (1.5H) 3.00; s (1.5H) 2.92; t (2H) 2.79; m (2H) 2.60; s (3H) 2.44; m (2H) 1.52; s (18H) 1.28; t (3H) 0.90.

D] Starting from the compound under C] (21.3 g, 71 mmoles) and lithium aluminium hydride (4.3 g, 107 mmoles) and substantially proceeding as in Example 10,B], after purification there were obtained 17.8 g of 5-(N-emthyl-N-dodecylamino)-2-pentanol.

$^1$H-NMR: m (1H) 3.71; m (4H) 2.38; s (3H) 2.23; m (6H) 1.83–1.39; s (18H) 1.28; d (3H) 1.18; t (3H) 0.90.

E] Methyl-triflate (0.76 ml, 6.9 mmoles) was slowly added to a solution of CDI (0.56 g, 3.5 mmoles) in nitromethane (6 ml). The reaction mixture was stirred at room temperature for 1 hour under nitrogen, then dropped into a solution of the compound under D] (2 g, 6.9 mmoles) in THF (20 ml). The reaction was stirred at room temperature for 24 hours, then the solvents were evaporated under vacuum and the crude dissolved in diethyl ether (50 ml). The roganic phase was washed with water, anhydrified over sodium sulfate and evaporated under vacuum. the resulting crude was purified by silica gel column chromatography (eluent: toluene/ethanol/ammonia 15:1:1) yielding 160 mg (yield: 10%) of di-5-(N-dodecyl-N-methyl)-2-pentyl carbonate.

| Elemental analysis: | C | H | N |
|---|---|---|---|
| calculated | 74.44 | 12.83 | 4.69 |
| found | 72.73 | 12.00 | 5.00 |

$^1$H-NMR: m(2H)4.76; m(8H)2.30; s(6H)2.18; m(54H)1.19 ÷ 1.69; t(6H)0.88
$^{13}$C-NMR: 154.72; 75.00(2C); 58.10(2C); 57.58 (2C); 42.37(2C); 33.97(2C); 32.07(2C); 29.88(2C); 29.80(8C); 29.51(2C); 27.77 (2C); 27.46(2C); 23.28(2C); 22.84(2C); 20.13(2C); 14.27(2C).

F] The compound under E] (120 mg, 0.2 mmoles) was dissolved in ethyl ether (50 ml) and added with a ether solution of 2N HCl (0.2 ml, 0.4 mmole). The solvent was evaporated and the resulting product was dissolved in chloroform and evaporated three times yielding 130 mg of the title product.

| Elemental analysis: | C | H | N | Cl |
|---|---|---|---|---|
| calculated | 66.34 | 11.73 | 4.18 | 10.58 |
| found | 65.32 | 11.53 | 4.21 | 10.28 |

$^1$H-NMR: m(2H)4.75; m(8H)3.09; s(6H)2.82; m(12H)1.58 ÷ 1.85; m(42H)1.18 ÷ 1.38; m(6H) 0.83.
$^{13}$C-NMR: 157.57; 77.62(2C); 57.78; 57.51; 57.42; 57.19; 43.88; 43.71; 34.98; 34.88; 32.69 (2C); 32.62(2C); 32.39(4C); 32.01(2C) 31.96(2C); 29.23(2C); 26.55; 26.45; 25.55 (2C); 22.43(2C); 22.33(2C); 22.12(2C); 16.82(2C).

EXAMPLE 48–56

The carbonate as a free base was dissolved in methanol and added with a methanol solution containing 2 equivalents of the desired acid. The solvent was evaporated under vacuum and the resulting crude was tritured with diethyl ether thus yielding the desired compound after filtration.

Di-4-(N,N-dibutylamino)-butyl carbonate dimethanesulfonate hydrate

| Elemental analysis: | C | H | N | S |
|---|---|---|---|---|
| calculated | 50.76 | 9.78 | 4.38 | 10.04 |
| found | 51.47 | 10.11 | 4.36 | 9.80 |

$^1$H-NMR: m(4H)4.15; m(12H)3.09; s(6H)2.73; m (16H)1.76 ÷ 1.53; m(8H)1.31; t(12H) 0.87.
$^{13}$C-NMR: 158.59; 70.53(2C); 55.56(4C); 54.99(2C); 41.33(2C); 28.05(4C); 27.90(2C); 22.70 (2C); 22.13(4C); 15.67(4C).

Di-(2-(N,N-dibutylamino)-1-cyclohexyl] carbonate sulfate hydrate

| Elemental analysis: | C | H | N | S |
|---|---|---|---|---|
| calculated | 58.36 | 10.13 | 4.69 | 5.37 |
| found | 57.55 | 10.35 | 4.50 | 4.97 |

$^1$H-NMR: m(2H)4.94; m(2H)3.57; m(8H)3.35 ÷ 2.87; m (4H)2.32 ÷ 2.03; m(28H)1.88 ÷ 1.20; t(6H) 0.88; t(6H)0.87.
$^{13}$C-NMR: 155.94; 78.29(0.6C); 78.11(1.4C); 66.48 (1.4C); 66.25(0.6C); 55.46(0.6C); 54.98 (1.4C); 53.58(0.6C); 53.23(1.4C); 33.37 (0.6C); 33.27(1.4C); 29.87(0.6C); 29.76 (1.4C); 29.19(1.4C); 29.02(0.6C); 26.06 (0.6C); 25.98(1.4C); 25.49(1.4C); 25.27 (0.6C); 25.22(1.4C); 25.09(0.6C); 22.32 (4C); 15.61(4C).

Di-(N-butyl-3-piperidylmethyl) carbonate camphosulfonate hydrate

| Elemental analysis: | C | H | N | S |
|---|---|---|---|---|
| calculated | 57.86 | 8.76 | 3.29 | 7.53 |
| found | 57.17 | 9.04 | 3.27 | 7.49 |

$^1$H-NMR: m(4H)4.07; m(4H)3.48; d(2H)3.21; m(4H) 3.04; d(2H)2.79; m(4H)2.88 ÷ 2.66; m(32H) 2.43 ÷ 1.21; s(6H)0.97; t(6H)0.86; s(6H) 0.77.
$^{13}$C-NMR: 224.72(2C); 158.19; 72.21(2C); 62.23(2C); 60.00(2C); 56.92(2C); 55.50(2C); 51.04 (2C); 49.97(2C); 45.41(2C); 45.09(2C); 36.56(2C); 29.05(2C); 28.35(2C); 27.37 (2C); 26.86(2C); 24.77(2C); 22.15(2C); 21.72(2C); 21.56(2C); 15.63(2C).

Di-5-(N,N-diisopropylamino)-pentyl carbonate di-4-toluensulfonate

| Elemental anaiysis: | C | H | N | S |
|---|---|---|---|---|
| calculated | 59.65 | 8.66 | 3.76 | 8.61 |
| found | 59.29 | 9.15 | 3.78 | 8.78 |

$^1$H-NMR: m(4H)7.61; m(4H)7.28; m(4H)4.08; m(4H) 3.58; m(4H)2.97; s(6H)2.31; m(8H)1.61; m(4H)1.35; d(24H)1.23.

-continued

| $^{13}$C-NMR: | 158.81; 145.24(2C); 142.41(2C); 132.29 (4C); 128.23(4C); 71.15(2C); 57.69(4C); 50.09(2C); 30.16(2C); 29.69(2C); 25.27 (2C); 23.35(2C); 19.82(8C). |
|---|---|

Di-5-(N,N-diisopropylamino)-pentyl carbonate di-4-benzenesulfonate hydrate

| Elemental analysis: | C | H | N | S |
|---|---|---|---|---|
| calculated | 57.20 | 8.50 | 3.81 | 8.72 |
| found | 58.35 | 9.02 | 3.70 | 8.50 |

| $^1$H-NMR: | m(4H)7.79 ÷ 7.72; m(6H)7.58 ÷ 7.43; m(4H) 4.11; m(4H)3.62; m(4H)3.02; m(8H)1.66; m(4H)1.39; d(24H)1.26. |
|---|---|
| $^{13}$C-NMR: | 158.88; 145.14(2C); 134.43(2C); 131.84 (4C); 128.19(4C); 71.14(2C); 57.71(4C); 50.10(2C); 30.16(2C); 29.68(2C); 25.26 (2C); 19.82(8C). |

Di-(N-butyl-3-piperidylmethyl) carbonate di-4-toluensulfonate hydrate

| Elemental analysis: | C | H | N | S |
|---|---|---|---|---|
| calculated | 58.96 | 7.92 | 3.93 | 8.99 |
| found | 58.98 | 8.79 | 3.92 | 8.69 |

| $^1$H-NMR: | m(4H)7.63; m(4H)7.30; m(4H)4.05; m(4H) 3.48; m(4H)2.82 ÷ 2.61; s(6H)2.33; m(2H) 2.15; m(10H)2.01 ÷ 1.53; m(6H)1.28; t(6H) 0.85. |
|---|---|
| $^{13}$C-NMR: | 158.04; 145.19(2C); 142.30(2C); 138.28 (4C); 128.21(4C); 72.21(2C); 60.25(2C); 57.07(2C); 55.59(2C); 36.82(2C); 28.25 (2C); 26.82(2C); 25.06(2C); 23.43(2C); 22.11(2C); 15.60 (2C). |

Di-(N-butyl-3-piperidylmethyl) carbonate dibenzensulfonate

| Elemental analysis: | C | H | N | S |
|---|---|---|---|---|
| calculated | 57.87 | 7.65 | 4.09 | 9.36 |
| found | 57.22 | 7.83 | 3.80 | 8.68 |

| $^1$H-NMR: | m(4H)7.77 ÷ 7.71; m(6H)7.53 ÷ 7.42; m(4H) 4.02; m(4H)3.45; m(4H)2.97; m(4H) 2.78 ÷ 2.57; m(2H)2.12; m(10H)1.95 ÷ 1.49; m (6H)1.34 ÷ 1.06; t(6H)0.82. |
|---|---|
| $^{13}$C-NMR: | 158.10; 145.28(2C); 134.42(2C); 131.86 (4C); 128.21(4C); 79.19(2C); 60.22(2C) 57.08(2C); 55.56(2C); 36.79(2C); 28.21 (2C); 26.80(2C); 25.03(2C); 22.10(2C); 15.61(2C). |

Di-(N-butyl-3-piperidylmethyl) carbonate sulfate

| Elemental analysis: | C | H | N | S |
|---|---|---|---|---|
| calculated | 55.05 | 9.07 | 6.00 | 6.87 |
| found | 53.70 | 9.91 | 5.70 | 6.49 |

-continued

| $^1$H-NMR: | m(4H)4.07; m(4H)3.48; m(4H)3.04; m(4H) 2.88 ÷ 2.68; m(2H)2.19; m(10H)1.98 ÷ 1.56; m (6H)1.40 ÷ 1.17; t(6H)0.86. |
|---|---|
| $^{13}$C-NMR: | 158.16; 72.23(2C); 59.91(2C); 56.89(2C); 55.47(2C); 36.52(2C); 28.30(2C); 26.86 (2C); 24.73(2C); 22.15(2C); 15.63(2C). |

Di-5-(piperidyl)-2-pentyl carbonate sulfate hydrate

| Elemental analysis: | C | H | N | S |
|---|---|---|---|---|
| calculated | 52.04 | 9.15 | 5.78 | 6.62 |
| found | 53.52 | 9.56 | 5.61 | 6.40 |

| $^1$H-NMR: | m(2H)4.74; m(4H)3.51 ÷ 3.38; m(4H)3.03; m (4H)2.85; m(20H)1.93 ÷ 1.34; d(6H)1.22. |
|---|---|
| $^{13}$C-NMR: | 157.72; 78.49; 78.42; 59.25(2C); 55.96(4C) 34.72(2C); 25.64(4C); 24.01(2C); 22.29 (2C); 21.69; 21.58. |

As already said, the compounds of the invention are useful as antiviral and anti-inflammatory agents.

TEST 1

Antiviral activity

The antiviral activity of the compound of the invention was evaluated by the test of the syncytia formation inhibition, according to the procedure reported hereinbelow.

8E51 Cells permanently infected with LAV (Lymphotropic Adenopathy Virus) defective of the pol gene, and MOLT3 cells (CD4+ human T-lymphoblastoid strain), cultured in RPMI 1640 medium with 10% calf fetal serum were co-incubated in a ratio of 1:2, at a concentration of $10^6$ cells/ml, and put in 96-conic shaped bottom wells Microtiter plates. The cells were added with some compounds representative of the invention suitably diluted and, after 30 minutes at 37° C., the whole was centrifuged to obtain a sediment. The supernatant was incubated for further 2 hours at 37° C., then put in square-bottomed wells. The syncytia (10–100 times bigger than the starting cells) were counted with an optic microscope. In the controls about 100–200 syncytia/well could be seen.

The results are set forth in Table 1.

TABLE 1

| | % of inhibition of syncytia | | | | |
|---|---|---|---|---|---|
| Example | 200 μM | 100 μM | 50 μM | 25 μM | 12.5 μM |
| 1, E] | 97 | 79 | 70 | 56.5 | |
| 4, C] | | 28 | 18 | | |
| 5, C] | | 23 | 22 | | |
| 8, D] | | 27 | 55 | 49 | 33 |
| 10, C] | | | 45.5 | 29.5 | |
| 13, E] | | 43.5 | 27.5 | | |
| 16, D] | | 27 | | | |
| 17, D] | | 19 | | | |
| 18, D] | | 63 | 55 | | |

TEST 2

In vitro anti-inflammatory activity

The anti-inflammatory activity of the compound of the invention was evaluated by the in vitro test of inhibition of the citotoxicity induced by human TNF (Tumor Necrosis Factor) on a murine fibroblast strain, as reported hereinbelow.

In a 96-square bottomed wells plate 15.000 LM cells (Rubin. B. Y. et al., J.Exp. Med., 162:1099, 1985) were inseminated each well (100 μl) in complete RPMI medium (Flow Lab., Hertz. GB). Each well was added with 50 μl of a solution of a compound to be tested at the due concentration, and 50 μl of a solution of TNF at the due concentration. After 2 days, each well was added with 40 μl of a solution of MTT [3-(4,5-dimethylthiazol-2-yl)-2,5-diphenyltetrazolium bromide], and the whole was incubated at 37° C. for 4 hours, then the content of the wells was sucked up, added with 200 μl/well of dimethylsulfoxide to dissolve the blue crystals of formazane formed because of the cell activity, then the optical density values were read by a reader with a 570 nm filter. The controls did not yield crystals. The optical density values are directly proportional to the inhibitory activity performed by the compounds of the invention against TNF.

TABLE 2

| Example | (μg/ml) | % of inhibition | |
|---|---|---|---|
| | | TNF (1 ng/ml) | TNF (5 ng/ml) |
| 1, E] | 100 | n.d. | n.d. |
| | 10 | 45 | n.d. |
| 2, C] | 100 | 90 | 43 |
| | 10 | 26 | n.d. |
| 4, C] | 100 | 23 | n.d. |
| | 10 | n.d. | n.d. |
| 5, C] | 100 | 36 | 30 |
| | 10 | 73 | 21 |
| 8, D] | 100 | 100 | 82 |
| | 10 | 100 | 56 |
| 10, C] | 100 | 100 | 95 |
| | 10 | 100 | 73 |
| 12, B] | 100 | 65 | 62 |
| | 10 | 68 | 50 |
| 13, E] | 100 | 45 | 21 |
| | 10 | 55 | n.d. |
| 14, E] | 100 | 100 | 59 |
| | 10 | n.d. | n.d. |
| 16, D] | 100 | n.d. | 21 |
| | 10 | n.d. | n.d. |
| 18, D] | 100 | 17 | n.d. |
| | 10 | n.d. | n.d. |
| 19, D] | 100 | 48 | n.d. |
| | 10 | 17 | n.d. | n.d.-not determined

TEST 3

In vivo anti-inflammatory activity: model of chronic inflammation

The cotton pellet granuloma test, discussed inter alia in J. Pharm. Pharmacol., 20, 305, 1968 was effected. Anaesthetized Wistar rats, weighing about 150 g, were shaved on the back. In the shaved zone a 1 cm-cut was made, then a sterilized cotton pellet weighing about 45 mg and containing 50 μl of an antibiotic was subcutaneously inserted. The cut was closed by means of a silk thread. After 30 minutes the rats were orally administered with 10, 30 or 100 mg/kg of the compounds of the invention. The administration was repeated for 8 days, then the animals were sacrificed, and the granuloma was taken off through a new cut and weighed after drying at 120° C. for 24 hours. The weight of the cotton pellet was subtracted from the ones of the granuloma. The compounds of the invention yielded a percentage of inhibition of the granuloma growth varying from about 25 to about 35% with respect to the control.

TEST 4

In vivo anti-inflammatory activity: models of acute inflammation

A. Carrageenan-induced oedema The test is disclosed, inter alia, by Blake, D. R. et al., Ann. Rheum. Dis., 43, 89–93, 1983. The animals were orally administered with 10 or 30 mg/kg doses of the compounds of the invention 1 hour before the injection of carrageenan. The condition of the oedema was checked 1, 3 and 5 hours after said injection. In Table 3 the percentage of reduction of the oedema is set forth.

TABLE 3

| Example | Dose mg/kg | % of inhibition | | |
|---|---|---|---|---|
| | | 1 hour | 3 hours | 5 hours |
| 10, C] | 10 | 26.1 | 10 | n.d. |
| | 30 | 13 | 43 | 31.3 |
| 18, D] | 30 | n.d. | 27 | 28.7 |
| 38, E] | 10 | 22.5 | 15 | 20.5 |

B. Phospholipase A2-induced oedema The test is disclosed, inter alia, by Masters, D. J. and Jacobs, V. N., Brit. J. Pharmacol., 102, 368P, 1991. After one night without food, the animals (8 each group) were orally treated with 30 or 100 mg/kg of one of the compounds of the invention. The controls were treated with 5 ml/kg of carboxymethyl cellulose only. After 60 minutes, the right hind paw was injected with 0.1 ml (100 U/ml) of phospholipase A2 (PLA2). The volume of such paw was plethysmographically measured 1 hour and 3 hours after the injection with the phlogistic agent. The results are expressed as percentage of inhibition of the oedema volume versus the control. The compounds of the invention yielded a percentage of inhibition ranging between about 30 and about 70% both at 1 hour and 3 hours after the injection of the phlogistic agent.

Object of the invention is also the use of the compounds of formula (I) and (I') as antiviral and antiinflammatory agents, and the industrial aspects connected to said use, together with their incorporation in pharmaceutical compositions. Examples of such Pharmaceutical compositions are tablets, sugar-coated and film-coated tablets, syrups and phails, the latter being suitable both for the oral and the parenteral administration. These contain the active principle alone or in combination with common carriers and pharmaceutically acceptable excipients. The doses of the active principle may vary within wide limits depending on the kind of the compound used which may be administered one or more times a day depending on the therapeutic needs.

We claim:

1. A method of treating a patient requiring anti-lymphotropic adenopathy viral therapy or anti-inflammatory therapy which comprises administering to said patient an effective dosage of a composition comprising as the principal active ingredient a compound of the formula

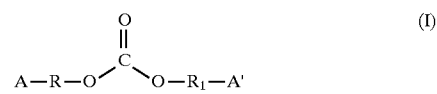
(I)

wherein

R and $R_1$ independently represent methylene, ethylene, $(C_{3-18})$alkylene optionally branched, $(C_{2-10})$alkylidene optionally branched, $(C_{5-7})$cycloalkylene, a group

wherein $R_2$ and $R_3$ are independently hydrogen or a $(C_{1-4})$alkyl group, and n and m are independently 0 or an integer from 1 to 6; and A and A' independently represent: the group $R_4$

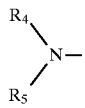

wherein $R_4$ and $R_5$ are independently hydrogen, or (C1–14)alkyl optionally branched, in admixture with a pharmaceutically acceptable carrier.

2. A method of treating a patient requiring anti-inflammatory therapy which comprises administering to said patient an effective dosage of a composition according to claim 1.

3. A method of treating a patient requiring anti-lymphotropic adenopathy viral therapy which comprises administering to said patient and effective dosage of a pharmaceutical composition comprising as the principal active ingredient an effective amount of di-5-(N,N-dibutylamino)-2-pentyl carbonate dihydrochloride hydrate in admixture with a pharmaceutically acceptable carrier.

* * * * *